(12) United States Patent
Shimuta et al.

(10) Patent No.: US 8,897,859 B2
(45) Date of Patent: Nov. 25, 2014

(54) BIOSENSOR DEVICE

(75) Inventors: Toru Shimuta, Kyoto-Fu (JP); Eiji Takahashi, Kyoto-Fu (JP)

(73) Assignee: Murata Manufacturing Co., Ltd., Nagaokakyo-Shi, Kyoto-fu (JP)

( * ) Notice: Subject to any disclaimer, the term of this patent is extended or adjusted under 35 U.S.C. 154(b) by 606 days.

(21) Appl. No.: 13/283,688

(22) Filed: Oct. 28, 2011

(65) Prior Publication Data

US 2012/0071734 A1 Mar. 22, 2012

Related U.S. Application Data

(63) Continuation of application No. PCT/JP2009/070539, filed on Dec. 8, 2009.

(30) Foreign Application Priority Data

Apr. 30, 2009 (JP) ................................. 2009-111045
Sep. 15, 2009 (JP) ................................. 2009-213363

(51) Int. Cl.
| | | |
|---|---|---|
| A61B 5/0205 | (2006.01) | |
| A61B 5/024 | (2006.01) | |
| A61B 5/00 | (2006.01) | |
| A61B 5/021 | (2006.01) | |
| A61B 5/1455 | (2006.01) | |
| A61B 5/0245 | (2006.01) | |
| A61B 5/0404 | (2006.01) | |
| A61B 5/0408 | (2006.01) | |

(52) U.S. Cl.
CPC ........... *A61B 5/0205* (2013.01); *A61B 5/02405* (2013.01); *A61B 5/6831* (2013.01); *A61B 5/6803* (2013.01); *A61B 5/4041* (2013.01); *A61B 5/02125* (2013.01); *A61B 5/1455* (2013.01); *A61B 5/0245* (2013.01); *A61B 5/0404* (2013.01); *A61B 5/0408* (2013.01); *A61B 5/6897* (2013.01); *A61B 5/6824* (2013.01)
USPC ......................................... 600/509; 600/513

(58) Field of Classification Search
USPC .......................................... 600/301, 509, 513
See application file for complete search history.

(56) References Cited

U.S. PATENT DOCUMENTS

| | | | |
|---|---|---|---|
| 3,882,846 A | 5/1975 | Fletcher et al. | |
| 5,749,367 A | 5/1998 | Gamlyn et al. | |

(Continued)

FOREIGN PATENT DOCUMENTS

| | | |
|---|---|---|
| CN | 1600269 A | 3/2005 |
| CN | 1723842 A | 1/2006 |

(Continued)

OTHER PUBLICATIONS

Supplementary European Search Report issued for counterpart application EP 09 84 4048, date of completion Sep. 26, 2013.

(Continued)

*Primary Examiner* — Carl H Layno
*Assistant Examiner* — Jennifer Ghand
(74) *Attorney, Agent, or Firm* — Dickstein Shapiro LLP

(57) ABSTRACT

A biosensor that includes a light transmissive electrocardiographic electrode and a light transmissive insulating film that detect an electrical signal relating to an electrocardiographic signal through capacitive coupling that are disposed above light emitting elements and a light receiving element that detect an optical detection signal relating to a photo-plethysmographic signal. When a user brings a finger into contact with a contact surface of the light transmissive insulating film, the electrical signal relating to the electrocardiographic signal is detected by the light transmissive electrocardiographic electrode. At the same time, reflected light emitted from the light emitting elements after being reflected from the user's finger are received by the light receiving element to detect an optical detection signal corresponding to the received reflected lights so that biological information is generated based on both the electrocardiographic signal and a photo-plethysmographic signal.

16 Claims, 19 Drawing Sheets

(56) References Cited

U.S. PATENT DOCUMENTS

| | | | |
|---|---|---|---|
| 6,243,651 B1 | 6/2001 | Masuo | |
| 7,149,571 B2 | 12/2006 | Maeda | |
| 7,197,351 B2 | 3/2007 | Umeda et al. | |
| 7,663,607 B2 | 2/2010 | Hotelling et al. | |
| 2003/0097078 A1* | 5/2003 | Maeda | 600/509 |
| 2004/0204637 A1* | 10/2004 | Diab et al. | 600/324 |
| 2005/0004482 A1 | 1/2005 | Drakulic | |
| 2005/0027203 A1* | 2/2005 | Umeda et al. | 600/509 |
| 2012/0022385 A1* | 1/2012 | Shimuta et al. | 600/509 |

FOREIGN PATENT DOCUMENTS

| | | |
|---|---|---|
| EP | 1 021 986 A2 | 7/2000 |
| JP | 62-079291 U | 5/1987 |
| JP | 4-276235 | 10/1992 |
| JP | 07-012384 | 1/1995 |
| JP | 7-0123348 | 1/1995 |
| JP | 11-512012 | 10/1999 |
| JP | 11-299740 A | 11/1999 |
| JP | 2000-107147 A | 4/2000 |
| JP | 2003-316824 A | 11/2000 |
| JP | 2003-144403 A | 5/2003 |
| JP | 2003-275186 A | 9/2003 |
| JP | 2005-046215 A | 2/2005 |
| JP | 2005-244121 A | 9/2005 |
| JP | 2006-158974 A | 6/2006 |
| JP | 2007-527261 A | 9/2007 |
| JP | 2007-533044 A | 11/2007 |

OTHER PUBLICATIONS

PCT/JP2009/070539 International Search Report dated Jul. 1, 2010.
PCT/JP2009/070539 Written Opinion dated Jul. 1, 2010.

* cited by examiner

BIOSENSOR DEVICE

CROSS REFERENCE TO RELATED APPLICATIONS

The present application is a continuation of International application No. PCT/JP2009/070539, filed Dec. 8, 2009, which claims priority to Japanese Patent Application No. 2009-111045, filed Apr. 30, 2009, and Japanese Patent Application No. 2009-213363, filed Sep. 15, 2009, the entire contents of each of which are incorporated herein by reference.

FIELD OF THE INVENTION

The present invention relates to a biosensor device for detecting an electrocardiographic signal and a photo-plethysmographic signal of a living body, and for generating biological information based on the detected signals.

BACKGROUND OF THE INVENTION

In general, an electrocardiographic (electrocardiogram) signal obtained by differentially amplifying electrical signals, which are generated with motions of the cardiac muscle, and a photo-plethysmographic signal obtained by optically detecting the blood pulsation in the artery, which is caused with beat pulses, are used for diagnosis of cardiovascular diseases, etc.

Recently, a biosensor device has been developed which has the function of detecting the electrocardiographic signal and the photo-plethysmographic signal at the same time and obtaining biological information, e.g., a heart rate, an oxygen saturation, and a pulse-wave propagation time. In such a biosensor device, an optical probe for detecting the photo-plethysmographic signal is disposed on one or both of two electrodes for detecting electrical signals relating to the electrocardiographic signal. The optical probe includes a light emitter and a light receiver, which are mounted in recesses or holes formed in the surface of the electrode.

In that type of related-art biosensor device, when a user puts fingers on the surfaces of the electrodes, electrical signals are detected from the fingers through the electrodes, and an electrocardiographic signal is obtained from the detected electrical signals. Simultaneously, detection light is emitted to the finger from the light emitter mounted in the recess or the hole formed in the electrode surface, and reflected light after the detection light has been reflected at the finger is received by the light receiver mounted in the recess or the hole formed in the electrode surface. A photo-plethysmographic signal corresponding to the received reflected light is then obtained (see Patent Document 1).

On the other hand, for the purpose of increasing an SN (Signal to Noise) ratio of the photo-plethysmographic signal obtained from the user's finger, it is desirable to restrict divergence of the detection light emitted from the light emitter, and to effectively collect the detection light toward the user's finger that is put on the electrode.

As a manner for collecting light emitted from a light emitting diode in a particular direction, there is known a technique of providing, on a substrate, a reflector having a concave reflecting surface, and mounting the light emitting diode at the bottom of a concave recess of the reflector (see Patent Document 2). Further, there is known a technique of providing a metal ring on the substrate in surrounding relation to the light emitting diode, forming a fillet portion made of an Ag (silver)-based brazing alloy along an inner peripheral surface of the ring, and utilizing the fillet portion as a light reflecting surface (see Patent Document 3).

Patent Document 1: Japanese Unexamined Patent Application Publication No. 2006-158974
Patent Document 2: Japanese Unexamined Utility Model Application Publication No. 62-79291
Patent Document 3: Japanese Unexamined Patent Application Publication No. 2005-244121

Meanwhile, one conceivable approach for promoting a size reduction of a biosensor device, which can detect the electrocardiographic signal and the photo-plethysmographic signal at the same time, is to reduce the size of each of the electrodes for detecting the electrical signals relating to the electrocardiographic signal. However, when the electrode size is reduced, contact between a living body (such as a user's finger) and the electrode become unstable and the SN ratio of the electrocardiographic signal is reduced.

Another conceivable approach for promoting the size reduction of the biosensor device is to shorten the distance between the light emitter and the light receiver for detecting the photo-plethysmographic signal. However, when the distance between the light emitter and the light receiver is shortened, the SN ratio of the photo-plethysmographic signal is reduced.

In more detail, the reflected light received by the light receiver contains reflected light having passed through the artery under the skin of the living body, and reflected light having been reflected at an outer surface of the skin of the living body. The reflected light having passed through the artery under the skin of the living body contains a pulse component of the artery blood, and an AC signal component corresponding to the pulse component is used as the photo-plethysmographic signal. On the other hand, the reflected light having been reflected at the outer surface of the skin of the living body does not contain the pulse component of the artery blood, and a signal component corresponding to the relevant reflected light is almost a DC component.

When the distance between the light emitter and the light receiver is shortened, a ratio of the reflected light having passed through the artery under the skin of the living body to the reflected light having been reflected at the outer surface of the skin of the living body is relatively reduced in the reflected light received by the light receiver. As a result, a ratio of the AC signal component useful as the photo-plethysmographic signal to the DC signal component not useful as the photo-plethysmographic signal is relatively reduced in an electrical signal that is obtained by converting the reflected light received by the light receiver. Hence, an influence of noise upon the photo-plethysmographic signal is increased and the SN ratio of the photo-plethysmographic signal is reduced.

In the related-art biosensor device disclosed in the above-cited Patent Document 1, because the light emitter and the light receiver are mounted in the recesses or the holes formed in the electrode surface, the electrode surface includes a concave-convex configuration and the concave-convex configuration makes unstable the contact between the user's finger, for example, and the electrode. This raises a risk that the SN ratio of the electrocardiographic signal may be reduced. Further, in the related-art biosensor device, because a light emitting portion of the light emitter and a light receiving portion of the light receiver are exposed at the electrode surface, it is difficult to protect those exposed portions against externally applied friction and shocks.

Additionally, as described above, for the purpose of increasing the SN ratio of the photo-plethysmographic signal obtained from, e.g., the user's finger, it is desirable to restrict divergence of the detection light emitted from the light emitter, and to effectively collect the detection light toward the user's finger that is put on the electrode.

However, when trying to realize the above point by providing the reflector or the ring on the substrate as disclosed in the above-mentioned related art, an area of the substrate is increased and a difficulty arises in reducing the size of the biosensor device. Further, because a step of providing the reflector or the ring on the substrate needs to be added to a manufacturing process for the biosensor device, and the manufacturing cost of the biosensor device is increased.

When the technique of forming a fillet portion made of an Ag (silver)-based brazing alloy along an inner peripheral surface of the ring is employed as disclosed in the above-cited Patent Document 3, heat treatment at high temperature of 600° C. or higher is required to form the fillet portion. Hence, the following problems occur. The disclosed technique cannot be applied to a printed circuit board, for example. The blazing has to be carried out before mounting elements, which constitute an electrical circuit, on the substrate. Equipment for high-temperature heat treatment is required.

SUMMARY OF THE INVENTION

The present invention has been accomplished in view of the above-described problems, etc., and an object of the present invention is to provide a biosensor device, which has a small size and which can simultaneously obtain an electrocardiographic signal and a photo-plethysmographic signal from a living body.

To achieve the above object, the present invention provides a biosensor device comprising at least one pair of electrocardiographic electrodes for detecting electrical signals of a living body, insulating films disposed on the at least one pair of electrocardiographic electrodes and having one surfaces, which are positioned oppositely away from the other surfaces being in contiguity with the at least one pair of electrocardiographic electrodes and which serve as contact surfaces to be contacted with the living body, a light emitter for emitting light to the living body, a light receiver for receiving the light emitted from the light emitter after being reflected by the living body, and a processing circuit including an electrocardiographic signal detection unit for generating an electrocardiographic signal by differentially amplifying the electrical signals of the living body, which are detected through capacitive coupling between the living body contacted with the contact surfaces of the insulating films and the at least one pair of electrocardiographic electrodes, and a photo-plethysmographic signal detection unit for generating a photo-plethysmographic signal based on the light emitted from the light emitter and the light received by the light receiver, wherein at least one of the at least one pair of electrocardiographic electrodes is a light transmissive electrocardiographic electrode made of an electroconductive material having light transparency in a wavelength range of the light emitted from the light emitter, the insulating film disposed on the light transmissive electrocardiographic electrode is a light transmissive insulating film made of an insulating material having light transparency in the wavelength range of the light emitted from the light emitter, the living body is illuminated with the light emitted from the light emitter through the light transmissive electrocardiographic electrode and the light transmissive insulating film, and the light reflected by the living body is received by the light receiver.

With the present invention described above, when a user brings, e.g., the thumbs or the forefingers of both hands into contact with the contact surface of the light transmissive insulating film on the light transmissive electrocardiographic electrode and with the contact surface of the insulating film on the other electrocardiographic electrode, respectively, an electrical signal is detected from one finger through capacitive coupling between the one finger and the light transmissive electrocardiographic electrode, and an electrical signal is detected from the other finger through capacitive coupling between the other finger and the other electrocardiographic electrode. The electrocardiographic signal can be obtained by differentially amplifying those two electrical signals.

Also, the light emitted from the light emitter passes through the light transmissive electrocardiographic electrode and the light transmissive insulating film for illumination of the user's finger contacted with the contact surface of the light transmissive insulating film. Further, the light emitted toward the user's finger is reflected by the user's finger. After passing through the light transmissive insulating film and the light transmissive electrocardiographic electrode, the reflected light is received by the light receiver. The light receiver outputs an optical detection signal corresponding to the received light. The photo-plethysmographic signal can be obtained from the optical detection signal.

Thus, since the living body is illuminated with the light emitted from the light emitter through the light transmissive electrocardiographic electrode and the light transmissive insulating film and the light reflected by the living body is received by the light receiver, the electrocardiographic signal and the photo-plethysmographic signal can be obtained at the same time. Further, since the light transmissive electrocardiographic electrode and the light transmissive insulating film for obtaining the electrocardiographic signal can be arranged in vertically overlapped relation to the light emitter and the light receiver for obtaining the photo-plethysmographic signal, the size of the biosensor device can be reduced while the size of the electrocardiographic electrode is set to be sufficiently large and the distance between the light emitter and the light receiver is set to be sufficiently long. It is hence possible to not only increase an SN ratio of each of the electrocardiographic signal and the photo-plethysmographic signal, but also to reduce the size of the biosensor device.

Moreover, since the light emitter and the light receiver can be arranged under the light transmissive electrocardiographic electrode, there is no need of forming, in the electrode surface, recesses or holes for mounting the light emitter and the light receiver unlike the related art. Therefore, the surfaces of the electrodes can be formed flat and more stable contact can be ensured between the user's finger and each of the electrode surfaces. As a result, the SN ratio of the electrocardiographic signal can be increased.

In addition, since the light emitter and the light receiver can be arranged under the light transmissive electrocardiographic electrode and the light transmissive insulating film, the light transmissive electrocardiographic electrode and the light transmissive insulating film can be utilized as covers for protecting the light emitter and the light receiver. Accordingly, the light emitter and the light receiver can be protected against externally applied friction and shocks.

In the biosensor device according to the present invention, the light emitter includes at least two light emitting elements emitting lights in different wavelength ranges.

With the present invention described above, since at least two light emitting elements emitting lights in different wavelength ranges are provided, the oxygen saturation of the living body can be measured.

In the biosensor device according to the present invention, the light emitter, the light receiver, and at least part of components constituting the processing circuit are mounted on a base plate, the at least part of the components is arranged around each of the light emitter and the light receiver, a peripheral wall reflector for reflecting light by a solder fillet, which is formed when the at least part of the components is mounted on the base plate, is formed around each of the light emitter and the light receiver.

With the present invention described above, the light emitted from the light emitter can be reflected by the peripheral wall reflector provided around each of the light emitter and the light receiver toward the living body (e.g., the user's finger), whereby the light can be effectively collected for illumination of the living body. Further, the light reflected by the living body can be reflected by the peripheral wall reflector toward the light receiver, whereby the light can be effectively collected for reception by the light receiver. As a result, the SN ratio of the photo-plethysmographic signal obtained from the living body can be increased.

Moreover, since the peripheral wall reflector is formed by the solder fillet that is formed on the component arranged around the light emitter and the light receiver, there is no need of separately adding a component dedicated for forming the peripheral wall reflector. It is hence possible to reduce the size of the biosensor device and to reduce the manufacturing cost of the biosensor device.

In the biosensor device according to the present invention, the at least one pair of electrocardiographic electrodes are connected to input terminals of the electrocardiographic signal detection unit for differentially amplifying the electrical signals of the living body, which are detected through capacitive coupling between the living body and the at least one pair of electrocardiographic electrodes, at least one clamp circuit including at least one high-impedance element is connected to each of the input terminals of the electrocardiographic signal detection unit, a potential at a connected end of the clamp circuit is fixedly held constant, and an impedance when looking at the electrocardiographic signal detection unit from the connected end of the clamp circuit is set to be larger than an impedance of the clamp circuit.

In trying to detect the electrical signal of the living body through the capacitive coupling between the electrocardiographic electrode and the living body, if the input impedance when looking at the electrocardiographic signal detection unit from the electrocardiographic electrode is low, a loss in a frequency band of the electrical signal of the living body is increased and the electrocardiographic signal cannot be detected.

In contrast, with the present invention described above, since the clamp circuit is constituted by using the high-impedance element and the impedance when looking at the input terminal of the electrocardiographic signal detection unit from the connected end of the clamp circuit is set to be larger than the impedance of the clamp circuit, the loss in the frequency band of the electrical signal of the living body can be reduced. Further, since the reference potential at the input terminal of the electrocardiographic signal detection unit can be fixedly held by the clamp circuit, variations in a central potential of the electrical signal of the living body can be reduced. As a result, the SN ratio can be increased and the electrical signal of the living body can be stably detected.

In the biosensor device according to the present invention, at least one of the at least one pair of electrocardiographic electrodes and the processing circuit are contained in a first housing, an insulating film to be contacted with a first portion of the living body is disposed in and exposed at a surface of the first housing in opposing relation to the electrocardiographic electrode contained in the first housing, at least one electrocardiographic electrode other than the electrocardiographic electrode contained in the first housing is contained in a second housing and is electrically connected to the processing circuit through a cable led out from the first housing, and another insulating film to be contacted with a second portion of the living body is disposed in and exposed at a surface of the second housing in opposing relation to the other electrocardiographic electrode.

With the present invention described above, an electrical signal at the first portion of the living body can be detected by the electrocardiographic electrode contained in the first housing. In addition, an electrical signal at the second portion of the living body can be detected by the other electrocardiographic electrode contained in the second housing. Further, the other electrocardiographic electrode is electrically connected to the processing circuit, which is contained in the first housing, through a cable led out from the first housing. Therefore, even when the first portion and the second portion of the living body where the electrical signals of the living body are easily detectable are at positions far away from each other, the electrocardiographic electrodes can be attached to the first and second portions, respectively, and detection accuracy of the electrical signals can be improved.

In the biosensor device according to the present invention, a light emitter for emitting light to the second portion of the living body and a light receiver for receiving the light emitted from the light emitter after being reflected by the living body are contained in the second housing in addition to the other electrocardiographic electrode electrically connected to the processing circuit through the cable, the other electrocardiographic electrode is a light transmissive electrocardiographic electrode made of an electroconductive material having light transparency in a wavelength range of the light emitted from the light emitter, the other insulating film disposed on the light transmissive electrocardiographic electrode is a light transmissive insulating film made of an insulating material having light transparency in the wavelength range of the light emitted from the light emitter, the second portion of the living body is illuminated with the light emitted from the light emitter through the light transmissive electrocardiographic electrode and the light transmissive insulating film, and the light reflected at the second portion of the living body is received by the light receiver.

With the present invention described above, the second housing contains the light emitter and the light receiver in addition to the other electrocardiographic electrode. Therefore, the photo-plethysmographic signal at the second portion of the living body can be obtained by using the light emitter and the light receiver.

Also, the present invention provides a biosensor device comprising at least one pair of electrocardiographic electrodes for detecting electrical signals of a living body, insulating films disposed on the at least one pair of electrocardiographic electrodes and having one surfaces, which are positioned oppositely away from the other surfaces being in contiguity with the at least one pair of electrocardiographic electrodes and which serve as contact surfaces to be contacted with the living body, a light emitter for emitting light to the living body, a light receiver for receiving the light emitted from the light emitter after being reflected by the living body, and a processing circuit including an electrocardiographic signal detection unit for generating an electrocardiographic signal by differentially amplifying the electrical signals of the living body, which are detected through capacitive coupling between the living body contacted with the contact surfaces of the insulating films and the at least one pair of electrocardiographic electrodes, and a photo-plethysmographic signal detection unit for generating a photo-plethysmographic signal based on the light emitted from the light emitter and the light received by the light receiver, wherein the light emitter includes at least two light emitting elements emitting lights in different wavelength ranges; at least one of the at least one pair of electrocardiographic electrodes is a light transmissive electrocardiographic electrode made of an electroconductive material having light transparency in a wavelength range of the light emitted from each of the light emitting elements of the light emitter; the insulating film disposed on the light transmissive electrocardiographic electrode is a light transmissive insulating film made of an insulating material having light transparency in the wavelength range of the light emitted from each of the light emitting elements of the light emitter; the living body is illuminated with the light emitted from each of the light emitting elements of the light emitter through the light transmissive electrocardiographic electrode and the light transmissive insulating film, and the light reflected by the living body is received by the light receiver; the light emitting elements of the light emitter, the light receiver, and at least part of components constituting the processing circuit are mounted on a base plate, and the at least part of the components is arranged around the light emitting elements of the light emitter and the light receiver; a peripheral wall reflector for reflecting light by a solder fillet, which is formed when the at least part of the components is mounted on the base plate, is formed around each of the light emitting elements of the light emitter and the light receiver; the at least one pair of electrocardiographic electrodes are connected to input terminals of the electrocardiographic signal detection unit for differentially amplifying the electrical signals of the living body, which are detected through capacitive coupling between the living body and the at least one pair of electrocardiographic electrodes; at least one clamp circuit including at least one high-impedance element is connected to each of the input terminals of the electrocardiographic signal detection unit; and a potential at a connected end of the clamp circuit is fixedly held constant, and an impedance when looking at the electrocardiographic signal detection unit from the connected end of the clamp circuit is set to be larger than an impedance of the clamp circuit.

BRIEF DESCRIPTION OF THE DRAWINGS

in FIG. 11.

in FIG. 18.

DETAILED DESCRIPTION OF THE INVENTION

Embodiments of the present invention will be described below with reference to the attached drawings. At the outset, a first embodiment of the present invention is described with reference to FIGS. 1 to 9.

Figure 1:
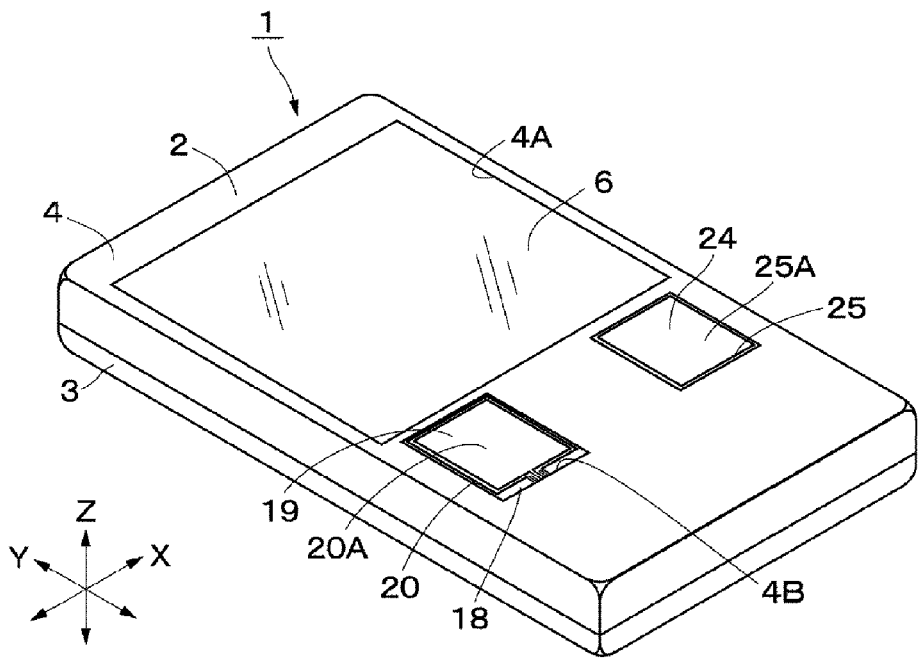
FIG. 1 is a perspective view of a biosensor device according to a first embodiment of the present invention.

In FIG. 1, a biosensor device 1 according to the first embodiment of the present invention can simultaneously detect an electrocardiographic signal and a photo-plethysmographic signal from the thumbs of both human hands, for example, and can generate biological information, such as an electrocardiogram, a heart rate, an oxygen saturation, and a pulse-wave propagation time, an acceleration plethysmogram, and a heart rate fluctuation, based on those signals. Further, the biosensor device 1 can estimate a blood pressure from the pulse-wave propagation time and a state of the automatic nerve from the heart rate fluctuation. A user can perform a versatile analysis of the health state by utilizing the biological information provided from the biosensor device 1. In addition, as seen from FIG. 2, the biosensor device 1 is a small-size, light-weight and portable device that can be readily lifted up by the user.

For the sake of convenience in explanation, the direction indicated by an arrow X in FIG. 1 is defined as a leftward and rightward direction. The direction indicated by an arrow Y in FIG. 1 is defined as a rearward and forward direction. The direction indicated by an arrow Z in FIG. 1 is defined as an upward and downward direction.

A housing 2 forms an outer shell of the biosensor device 1, and it is formed by using resin, for example. The housing 2 is made up of a lower case 3 covering a lower portion of the biosensor device 1, and an upper case 4 covering an upper portion of the biosensor device 1.

Figure 3:
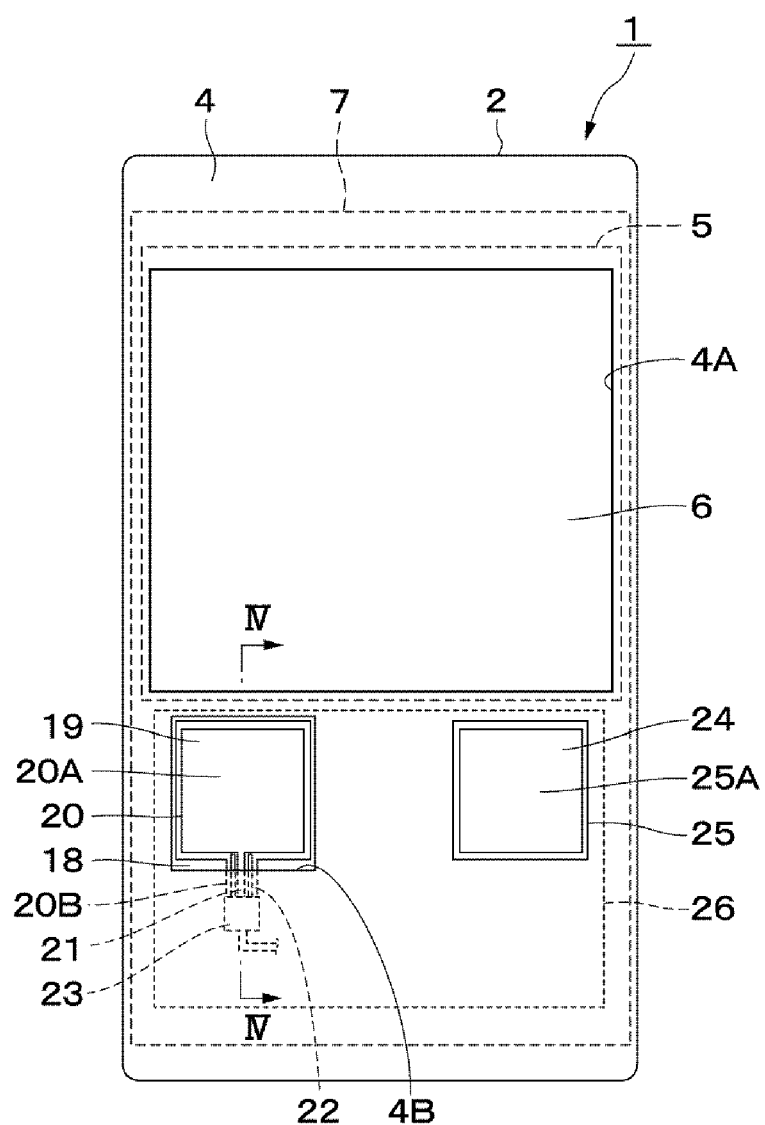
FIG. 3 is a front view of the biosensor device according to the first embodiment.

As illustrated in FIG. 3, a display panel 5 is disposed inside the housing 2 in a rearward-side portion thereof. An opening 4A allowing the user to view a display screen of the display panel 5 is formed in an upper surface of the upper case 4 in a rearward-side portion thereof, and a display window 6 in the form of a resin-made transparent plate is attached to the opening 4A.

Further, a light passing opening 4B having a square shape is formed in the upper surface of the upper case 4 in a forward left-side portion thereof, and an upper portion of a light transmissive sealing member 18 (described later) is fitted to the light passing opening 4B.

Figure 4:
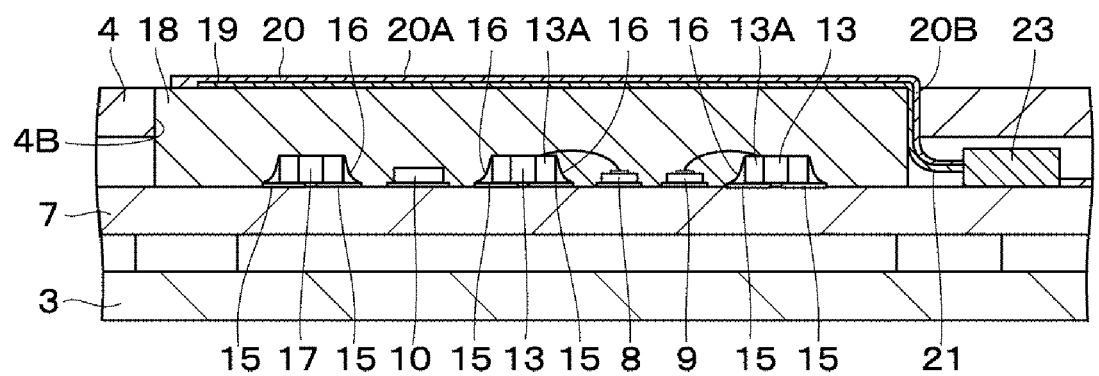
FIG. 4 is an enlarged longitudinal sectional view, taken along a line IV-IV in FIG. 3 in a direction denoted by arrow, illustrating a light transmissive electrocardiographic electrode, a light transmissive insulating film, a base plate, a light emitting element, a light receiving element, surface-mounted components, etc. in the biosensor device.

In FIGS. 3 and 4, a base plate 7 is disposed inside the housing 2. The base plate 7 is attached within the lower case 3. On the base plate 7, the display panel 5 is disposed in a rearward-side portion thereof, and light emitting elements 8 and 9, a light receiving element 10, a processing circuit 26 (each described below), etc. are mounted in a forward-side portion thereof.

In FIG. 4, two light emitting elements 8 and 9 are light emitters disposed on the base plate 7. The light emitting elements 8 and 9 are each constituted by, e.g., a light emitting diode (LED), and they serve to detect an optical detection signal, which is related to the photo-plethysmographic signal, from the user's finger in cooperation with the light receiving element 10 (described later). Stated another way, each of the light emitting elements 8 and 9 emits detection light for obtaining the optical detection signal to the user's finger that is contacted with a contact surface 20A of a light transmissive insulating film 20 (described later). A vertical cavity surface emitting laser (VCSEL) or a resonator-type LED may be used as each of light emitting elements 8 and 9.

The light emitting elements 8 and 9 are disposed under the light passing opening 4B formed in the upper case 4 in the forward left portion thereof. Further, the light emitting elements 8 and 9 are driven by a light emitting element driver 33 (light emitting element drive circuit 14) described later.

Further, the light emitting elements 8 and 9 emit detection lights having different wavelength ranges. For example, the light emitting element 8 emits detection light having a wavelength range where oxygenated hemoglobin exhibits a high absorbance, and the light emitting element 9 emits detection light having a wavelength range where deoxygenated hemoglobin exhibits a high absorbance.

The light receiving element 10 is a light receiver disposed on the base plate 7. The light receiving element 10 is constituted by, e.g., a photodiode. A phototransistor may also be used as the light receiving element 10. The light receiving element 10 is disposed under the light passing opening 4B. Further, the distance between the light receiving element 10 and each of the light emitting elements 8 and 9 is in the range of, e.g., 5 mm to 10 mm. The light receiving element 10 receives reflected light of the detection light emitted from each of the light emitting elements 8 and 9 (i.e., light resulting after the detection light has been reflected at the user's finger contacted with the contact surface 20A of the light transmissive insulating film 20), converts the received light to an optical detection signal, and outputs the optical detection signal to an optical detection signal amplifier 34 (see FIG. 9) of the processing circuit 26.

Figure 5:
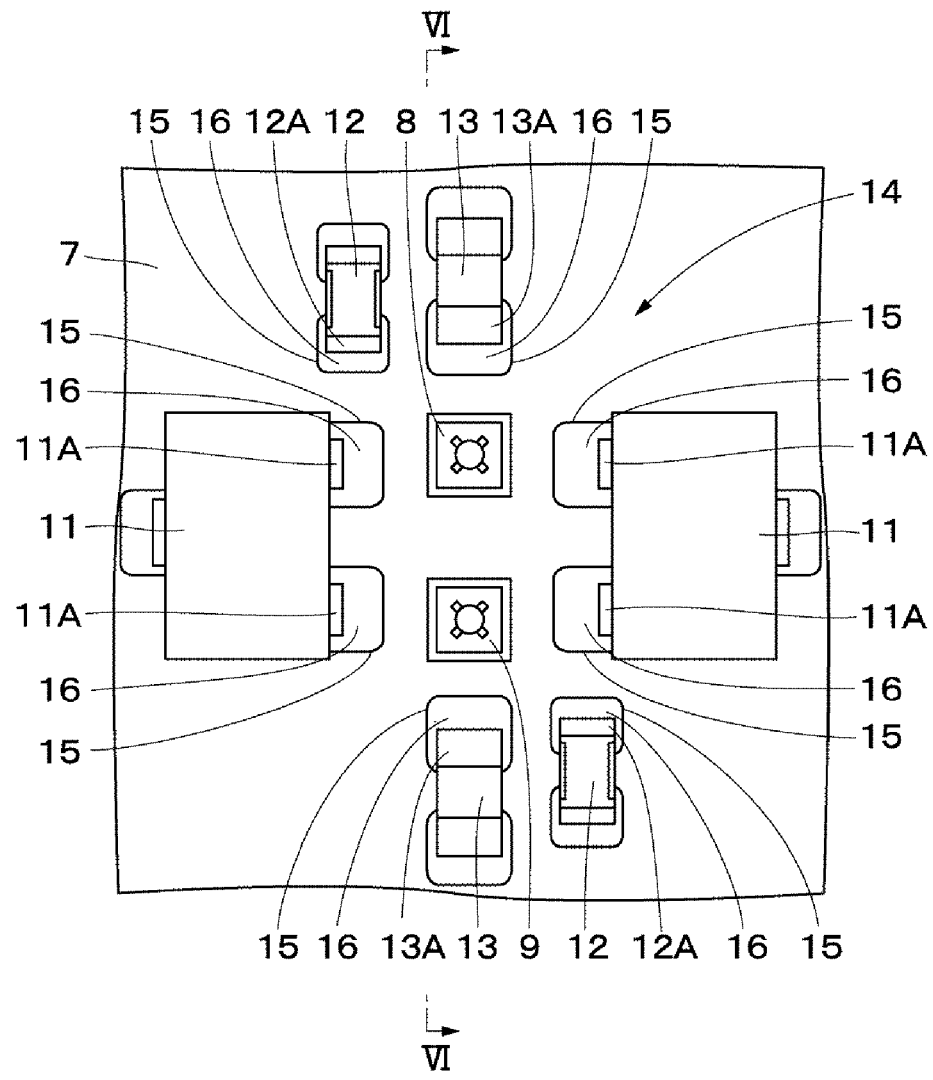
FIG. 5 is a front view illustrating the light emitting element and the surface-mounted components of the biosensor device according to the first embodiment with omission of a light transmissive sealing member, the light transmissive electrocardiographic electrode, and the light transmissive insulating film.
Figure 7:
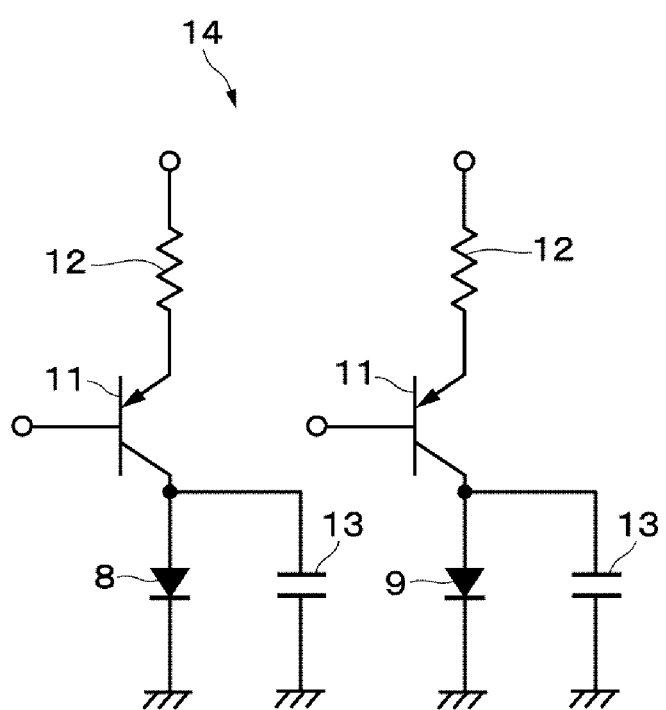
FIG. 7 is a circuit diagram of a light-emitting element drive circuit.

In FIG. 5, the surface-mounted components 11, 12 and 13 are respectively a transistor, a resistor, and a capacitor. The surface-mounted components 11, 12 and 13 constitute the light emitting element drive circuit 14 contained in the light emitting element driver 33 of the processing circuit 26. More specifically, as illustrated in FIG. 7, the surface-mounted components 11, 12 and 13 constitute the light emitting element drive circuit 14, which includes a constant-current circuit and a high-frequency cut-off filter circuit for driving the light emitting elements 8 and 9 and controlling the light emissions from the light emitting elements 8 and 9.

Figure 6:
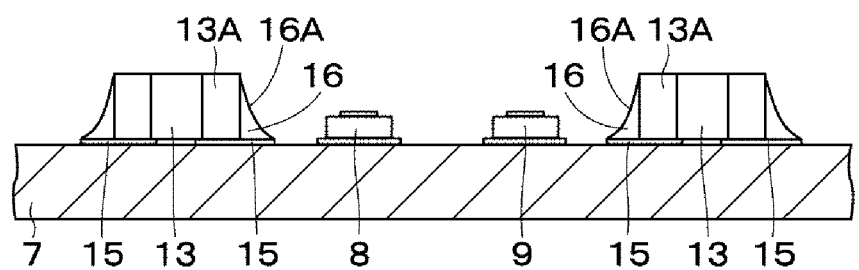
FIG. 6 is a sectional view, taken along a line VI-VI in FIG. 5 in a direction denoted by arrow, illustrating the light emitting element and the surface-mounted components.

The surface-mounted components 11, 12 and 13 are disposed on the base plate 7 near the light emitting elements 8 and 9 in surrounding relation to the light emitting elements 8 and 9, and they have connection terminals 11A, 12A and 13A at positions to face the light emitting elements 8 and 9. Further, as illustrated in FIG. 6, the surface-mounted components 11, 12 and 13 are fixed onto the base plate 7 (although FIG. 6 illustrates only the surface-mounted component 13) and are electrically connected to the light emitting elements 8 and 9, the processing circuit 26 (described later), etc. by soldering the connection terminals 11A, 12A and 13A to electrode pads 15 formed on the base plate 7.

Peripheral wall reflectors 16 are formed around the light emitting elements 8 and 9. The peripheral wall reflectors 16 are defined by solder fillets that are formed when mounting the surface-mounted components 11, 12 and 13 onto the base plate 7. In more detail, the electrode pads 15 for connection with the connection terminals 11A, 12A and 13A of the surface-mounted components 11, 12 and 13 are formed to extend toward the light emitting elements 8 and 9. Therefore, when the connection terminals 11A, 12A and 13A are soldered to the electrode pads 15, the solder fillets are formed between the connection terminals 11A, 12A and 13A and the electrode pads 15 due to wetting with a solder applied in the soldering step, and the peripheral wall reflectors 16 are formed by the solder fillets.

The solder fillets have slopes inclining obliquely downward from the connection terminals 11A, 12A and 13A toward the light emitting elements 8 and 9, and the slopes of the solder fillets serve as reflecting surfaces 16A of the peripheral wall reflectors 16. Inclination angles of the reflecting surfaces 16A, i.e., the slopes of the solder fillets, are desirably set to be in the range of about 30° to 60°, for example.

The reflecting surfaces 16A of the peripheral wall reflectors 16 reflect the detection lights emitted from the light emitting elements 8 and 9 toward the user's finger that is contacted with the contact surface 20A of the light transmissive insulating film 20. In more detail, the light emitting elements 8 and 9 emit most of the detection lights upward, but parts of the detection lights are diffused leftward, rightward, rearward, and forward in the surroundings of the light emitting elements 8 and 9. The diffused detection lights impinge upon the reflecting surfaces 16A of the peripheral wall reflectors 16. The directions of the diffused detection lights are thereby changed upward. As a result, the detection lights are collected to advance upward and to pass through the light passing opening 4B. Hence, the user's finger contacted with the contact surface 20A of the light transmissive insulating film 20 is illuminated with the detection lights at a higher degree of intensity.

As illustrated in FIG. 4, the peripheral wall reflectors 16 are also similarly formed around the light receiving element 10. In more detail, as illustrated in FIG. 4, the surface-mounted components 13 and 17, etc. constituting part of the processing circuit 26 are disposed around the light receiving element 10, and the peripheral wall reflectors 16 are defined by solder fillets that are formed when mounting the surface-mounted components 13 and 17, etc. onto the base plate 7. The peripheral wall reflectors 16 formed around the light receiving element 10 make reflection such that the detection lights after being reflected at the user's finger contacted with the contact surface 20A of the light transmissive insulating film 20 are directed to the light receiving element 10.

In FIG. 4, the light transmissive sealing member 18 seals off the light emitting elements 8 and 9, the light receiving element 10, the surface-mounted components 11, 12 13 and 17, etc. on the base plate 7. The light transmissive sealing member 18 is made of an insulating material having optical transparency in the wavelength ranges of the lights emitted from the light emitting elements 8 and 9, such as a transparent insulating resin. Stated another way, the light transmissive sealing member 18 entirely covers a region in the upper surface of the base plate 7, the region substantially corresponding to the shape of the light passing opening 4B in the upper case 4, thereby enclosing the light emitting elements 8 and 9, the light receiving element 10, the surface-mounted components 11, 12, 13 and 17, etc., which are disposed in the relevant region.

The upper portion of the light transmissive sealing member 18 is fitted to the light passing opening 4B. However, a gap for arranging a line protective portion 20B of the light transmissive insulating film 20, an electroconductive line 21, and ground lines 22 (each described later) is formed between a part of a forward-side end surface of the light transmissive sealing member 18 and a part of a forward-side inner peripheral surface of the light passing opening 4B.

The light transmissive sealing member 18 serves as a support for supporting a light transmissive electrocardiographic electrode 19 (described below) and the light transmissive insulating film 20 above the light emitting elements 8 and 9 and the light receiving element 10.

In FIG. 3, the light transmissive electrocardiographic electrode 19 is disposed on the light transmissive sealing member 18. The light transmissive electrocardiographic electrode 19 serves as an electrode for detecting an electrical signal relating to the electrocardiographic signal from the thumb of the user's left hand. The light transmissive electrocardiographic electrode 19 is made of an electroconductive material having optical transparency in the wavelength ranges of the lights emitted from the light emitting elements 8 and 9. For example, the light transmissive electrocardiographic electrode 19 is made of a transparent electroconductive metal material, e.g., ITO (Indium Tin Oxide), ZnO (Zinc Oxide), $SnO_2$ (Stannic (Tin) Oxide), $TiO_2$ (Titanium Oxide), or a magnesium-base nonoxide. Alternatively, it may be made of a transparent electroconductive resin. Further, the light transmissive electrocardiographic electrode 19 is disposed as a thin film having a thickness of about several μm to several tens μm on the upper surface of the light transmissive sealing member 18.

The light transmissive electrocardiographic electrode 19 is formed in a square shape with one side having a length of, e.g., about 10 mm to 30 mm. Alternatively, the light transmissive electrocardiographic electrode 19 may have a circular or elliptic shape with a diameter of about 10 mm to 30 mm. Further, as illustrated in FIG. 4, the light transmissive electrocardiographic electrode 19 is disposed above the light emitting elements 8 and 9 and the light receiving element 10.

The light transmissive insulating film 20 covers an upper surface of the light transmissive electrocardiographic electrode 19. The light transmissive insulating film 20 is made of an insulating material having optical transparency in the wavelength ranges of the lights emitted from the light emitting elements 8 and 9, such as a transparent insulating material, e.g., polyethylene naphthalate (PEN), polyethylene terephthalate (PET), or polyimide. The thickness of the light transmissive insulating film 20 is, e.g., several μm to several tens μm. Further, the light transmissive insulating film 20 covers not only the entire upper surface of the light transmissive electrocardiographic electrode 19, but also the surroundings of the light transmissive electrocardiographic electrode 19, thus shielding the light transmissive electrocardiographic electrode 19 against open air.

One surface of the light transmissive insulating film 20, which is positioned oppositely away from the other surface being in contiguity with the light transmissive electrocardiographic electrode 19, serves as the contact surface 20A to be contacted with the user's thumb. When the user's thumb is contacted with the contact surface 20A, an electrical signal relating to the electrocardiographic signal is detected from the user's thumb through capacitive coupling between the user's thumb and the light transmissive electrocardiographic electrode 19.

Figure 8:
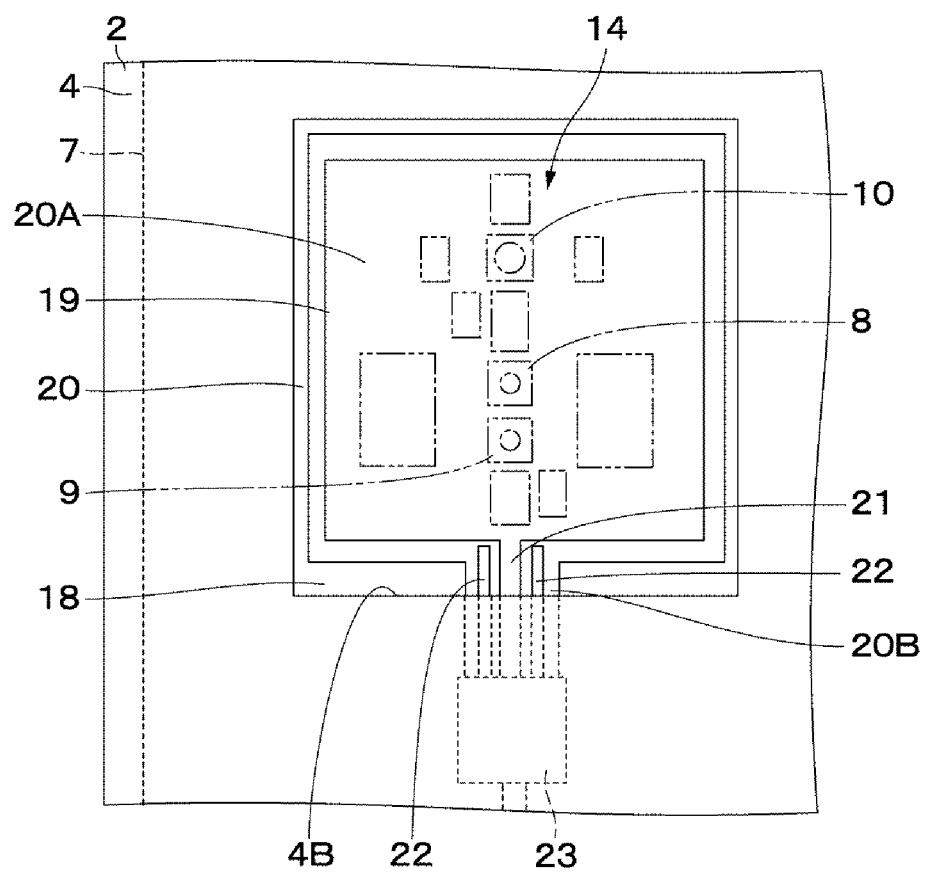
FIG. 8 is an enlarged view, taken in the same direction as that in the plan view of FIG. 3, illustrating the light transmissive electrocardiographic electrode, the light transmissive insulating film, etc. in the biosensor device.

Further, as illustrated in FIG. 3, the line protective portion 20B is disposed at a forward-side edge of the light transmissive insulating film 20 to protect the current carrying line 21 and the ground lines 22 (each described below). As illustrated in FIG. 8, the line protective portion 20B is formed by partly extending a forward-side edge portion of the light transmissive insulating film 20 toward a connector 23 (described later) that is disposed on the base plate 7. The line protective portion 20B covers respective surfaces of the current carrying line 21 and the ground lines 22.

The current carrying line 21 electrically connects the light transmissive electrocardiographic electrode 19 and a signal terminal of the connector 23. The current carrying line 21 is made, for example, of the same electroconductive material as that of the light transmissive electrocardiographic electrode 19. Further, as illustrated in FIGS. 4 and 8, the proximal end of the current carrying line 21 is connected to the light transmissive electrocardiographic electrode 19, while the distal end of the current carrying line 21 is extended downward together with the line protective portion 20B into the housing 2 after passing through the gap between the forward-side end surface of the light transmissive sealing member 18 and the forward-side inner peripheral surface of the light passing opening 4B. Further, the distal end of the current carrying line 21 is connected to the signal terminal of the connector 23.

The ground lines 22 are positioned on both the left and right sides of the current carrying line 21 and are arranged with a predetermined distance left from the current carrying line 21. The ground lines 22 are each made of an electroconductive material. Further, the ground lines 22 are each extended parallel to the current carrying line 21 from the proximal end side to the distal end side thereof, and the distal end of each ground line 22 is connected to a ground terminal of the connector 23. By surrounding the current carrying line 21 with the two ground lines 22 as described above, radiation noise can be effectively avoided from being superimposed on the electrical signal that flows through the current carrying line 21.

The connector 23 is disposed on the base plate 7. The connector 23 not only connects the current carrying line 21 to an electrocardiographic signal filter unit 28 of the processing circuit unit 26 (described later), which is disposed on the base plate 7, but also connects the ground lines 22 to a ground portion (not shown) provided on the base plate 7. Thus, the connector 23 includes a signal terminal (not shown) for connecting the current carrying line 21 and the electrocardiographic signal filter unit 28, and a ground terminal (not shown) for connecting the ground lines 22 and the ground portion provided on the base plate 7.

In FIG. 3, an electrocardiographic electrode 24 is disposed on the upper surface of the upper case 4 in a forward right portion thereof. The electrocardiographic electrode 24 serves as an electrode for detecting an electrical signal relating to the electrocardiographic signal from the thumb of the user's right hand. The electrocardiographic electrode 24 is made of an electroconductive material, and it has substantially the same thickness and size as those of the light transmissive electrocardiographic electrode 19. Further, the electrocardiographic electrode 24 is electrically connected to an electrocardiographic signal filter unit 29 of the processing circuit 26 through an electric wire (not shown).

To avoid radiation noise from being superimposed on the electrical signal detected by the electrocardiographic electrode 24, it is desirable that the electric wire for electrically connecting the electrocardiographic electrode 24 and the electrocardiographic signal filter unit 29 is covered with a conductor with a space or an insulator interposed therebetween, and that the conductor is grounded.

An insulating film 25 covers an upper surface of the electrocardiographic electrode 24. The insulating film 25 is made, for example, of a similar transparent insulating material to that of the light transmissive insulating film 20, and it has substantially the same thickness and size as those of the light transmissive insulating film 20. Further, the insulating film 25 covers not only the entire upper surface of the electrocardiographic electrode 24, but also the surroundings of the electrocardiographic electrode 24, thus shielding the electrocardiographic electrode 24 against open air.

One surface of the insulating film 25, which is positioned oppositely away from the other surface being in contiguity with the electrocardiographic electrode 24, serves as the contact surface 25A to be contact with the user's thumb. When the user's thumb is contacted with the contact surface 25A, an electrical signal relating to the electrocardiographic signal is detected from the user's thumb through capacitive coupling between the user's thumb and the electrocardiographic electrode 24.

The electrocardiographic electrode 24 may be buried in the forward right portion of the upper case 4 on the side closer to the user. In that case, a portion of the upper case 4, which is positioned above the buried electrocardiographic electrode 24, serves as an insulating film, and hence the insulating film 25 is not required.

Figure 9:
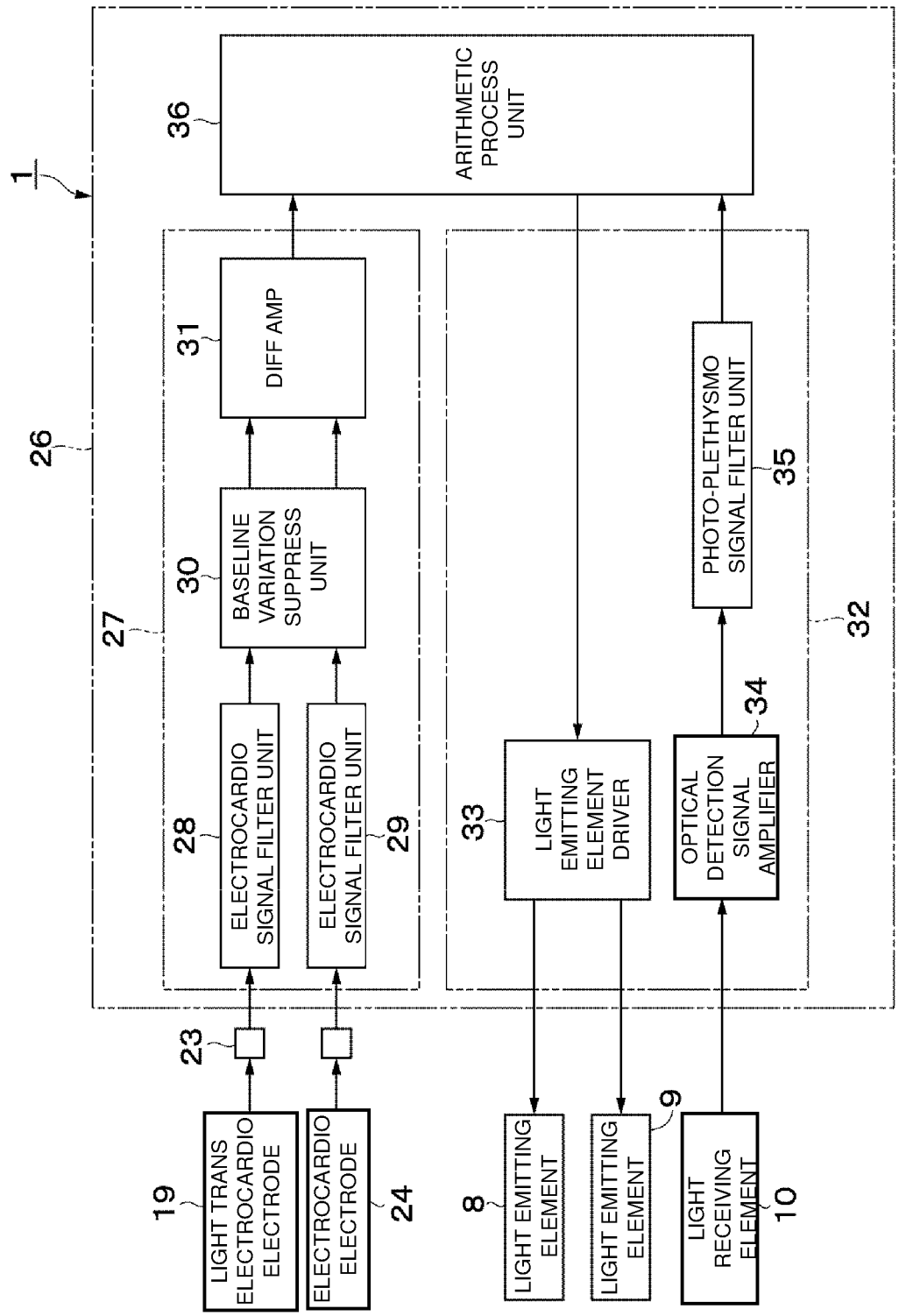
FIG. 9 is a block diagram illustrating the electrical configuration of the biosensor device according to the first embodiment.

The processing circuit 26 is disposed on the base plate 7. As illustrated in FIG. 9, the processing circuit 26 primarily includes an electrocardiographic signal detection unit 27, a photo-plethysmographic signal detection unit 32, and an arithmetic processing unit 36.

In more detail, the electrocardiographic signal detection unit 27 generates the electrocardiographic signal of the user. The electrocardiographic signal detection unit 27 includes two electrocardiographic signal filter units 28 and 29, a baseline variation suppression unit 30, and a differential amplifier 31.

The electrocardiographic signal filter unit 28 is connected to the light transmissive electrocardiographic electrode 19 through the current carrying line 21, the signal terminal of the connector 23, etc. Also, the electrocardiographic signal filter unit 29 is connected to the electrocardiographic electrode 24 in a substantially similar way. The electrocardiographic signal filter units 28 and 29 serve to reduce noises included in the electrical signals relating to the electrocardiographic signal, which have been detected from the thumbs of the user's both hands.

The electrocardiographic signal filter units 28 and 29 are each constituted by, e.g., a low-pass filter (LPF). Also, in order to reduce waveform distortion of the electrocardiographic signal generated by the differential amplifier 31, the input impedance of each of the electrocardiographic signal filter units 28 and 29 is desirably set relatively high, e.g., 1 GΩ to 10 TΩ.

The baseline variation suppression unit 30 is connected downstream of the electrocardiographic signal filter units 28 and 29. The baseline variation suppression unit 30 suppresses variations in respective baselines of the electrical signals relating to the electrocardiographic signal, which are output from the electrocardiographic signal filter units 28 and 29.

The differential amplifier 31 is connected downstream of the baseline variation suppression unit 30, and it is constituted by a differential amplification circuit including, e.g., an operational amplifier, etc. The input impedance of a generally used operational amplifier is 1 GΩ or more. Therefore, the input impedance of the differential amplifier 31 is 1 GΩ or more. The differential amplifier 31 differentially amplifies the electrical signals relating to the electrocardiographic signal, which are output from the baseline variation suppression unit 30, thereby generating the electrocardiographic signal. Stated another way, the differential amplifier 31 generates the electrocardiographic signal by differentially amplifying the electrical signal, which has been detected from the thumb of the user's left hand by the light transmissive electrocardiographic electrode 19 and which has been input to the differential amplifier 31 through the electrocardiographic signal filter unit 28 and the baseline variation suppression unit 30, and the electrical signal, which has been detected from the thumb of the user's right hand by the electrocardiographic electrode 24 and which has been input to the differential amplifier 31 through the electrocardiographic signal filter unit 29 and the baseline variation suppression unit 30.

On the other hand, the photo-plethysmographic signal detection unit 32 generates the photo-plethysmographic signal of the user in cooperation with the arithmetic processing unit 36. The photo-plethysmographic signal detection unit 32 includes the light emitting element driver 33, the optical detection signal amplifier 34, and a photo-plethysmographic signal filter unit 35.

The light emitting element driver 33 drives the light emitting elements 8 and 9 and controls the emission power and the timing of the detection lights emitted therefrom. The light emitting element drive circuit 14, illustrated in FIGS. 5 to 7, constitutes part of the light emitting element driver 33.

The optical detection signal amplifier 34 is connected to the light receiving element 10. The optical detection signal amplifier 34 executes current-voltage conversion of the optical detection signal supplied from the light receiving element 10 and amplifies the optical detection signal after the current-voltage conversion.

The photo-plethysmographic signal filter unit 35 is connected downstream of the optical detection signal amplifier 34, and it removes noise from the optical detection signal that is output from the optical detection signal amplifier 34. The photo-plethysmographic signal filter unit 35 includes a low-pass filter and, as required, a high-pass filter.

The arithmetic processing unit 36 is, e.g., a Central Processing Unit (CPU), and it executes, e.g., a process of controlling the detection lights emitted from the light emitting elements 8 and 9, a process of extracting the photo-plethysmographic signal from the optical detection signal, a process of generating biological information based on the electrocardiographic signal and the photo-plethysmographic signal, and overall control of the biosensor device 1.

In more detail, the arithmetic processing unit 36 supplies a first pulse control signal, i.e., a pulse signal for controlling the detection light from the light emitting element 8, and a second pulse control signal, i.e., a pulse signal for controlling the detection light from the light emitting element 9, to the light emitting element driver 33 such that the light emitting elements 8 and 9 are caused to emit pulse-like lights corresponding to the first and second pulse control signals, respectively. The pulse-like detection lights are thus emitted from the light emitting elements 8 and 9. Herein, the first pulse control signal and the second pulse control signal differ in phase from each other. Therefore, the emission timings of the detection lights from the light emitting elements 8 and 9 differ from each other.

Further, the arithmetic processing unit 36 executes the process of extracting the photo-plethysmographic signal from the optical detection signal that is supplied from the light receiving element 10 through the optical detection signal amplifier 34 and the photo-plethysmographic signal filter unit 35. The arithmetic processing unit 36 executes the extracting process as a time sharing process in synchronism with each cycle and phase of the first and second pulse control signals, thereby separating, from the optical detection signal, the photo-plethysmographic signal corresponding to the detection light from the light emitting element 8 and the photo-plethysmographic signal corresponding to the detection light from the light emitting element 9.

Moreover, the arithmetic processing unit 36 generates biological information, such as an electrocardiogram, a heart rate, an oxygen saturation, and a pulse-wave propagation time, an acceleration plethysmogram, and a heart rate variation, based on the photo-plethysmographic signals separated and extracted as described above and the electrocardiographic signal generated by the differential amplifier 31.

The operation of the above-described biosensor device 1 according to the first embodiment of the present invention will be described below.

Figure 2:
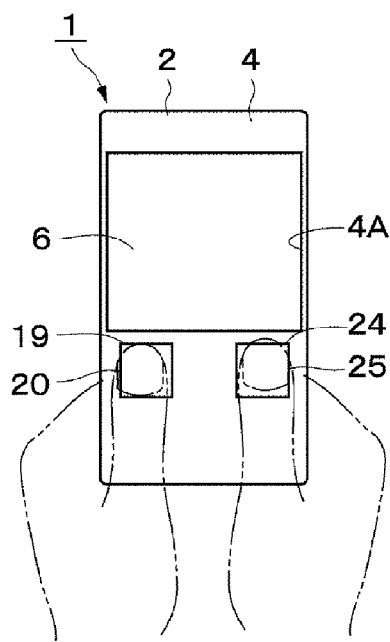
FIG. 2 is an explanatory view of the biosensor device according to the first embodiment in a state where a user is making measurement.

When the user brings the thumb of the left hand into contact with the contact surface 20A of the light transmissive insulating film 20 and brings the thumb of the right hand into contact with the contact surface 25A of the insulating film 25 as illustrated in FIG. 2, a first electrical signal relating to the electrocardiographic signal is detected by the light transmissive electrocardiographic electrode 19 through capacitive coupling between the thumb of the left hand and the light transmissive electrocardiographic electrode 19, and a second electrical signal relating to the electrocardiographic signal is detected by the electrocardiographic electrode 24 through capacitive coupling between the thumb of the right hand and the electrocardiographic electrode 24. The first electrical signal and the second electrical signal are differentially amplified by the differential amplifier 31 after their noises have been reduced respectively by the electrocardiographic signal filter units 28 and 29 and variations of their baselines have been suppressed by the baseline variation suppression unit 30. As a result, the electrocardiographic signal of the user is obtained and supplied to the arithmetic processing unit 36.

Simultaneously, the first and second pulse control signals are supplied from the arithmetic processing unit 36 to the light emitting element driver 33. In response to the first and second pulse control signals, the light emitting elements 8 and 9 emit the detection lights in the different wavelength ranges at the different emission timings. The emitted detection lights reach the thumb of the user's left hand through the light transmissive sealing member 18, the light transmissive electrocardiographic electrode 19, and the light transmissive insulating film 20. The reflected lights after the detection lights have been reflected at the thumb of the user's left hand reach the light receiving element 10 through the light transmissive insulating film 20, the light transmissive electrocardiographic electrode 19, and the light transmissive sealing member 18. The light receiving element 10 receives the reflected lights and outputs the optical detection signal corresponding to the reflected lights. The optical detection signal is amplified by the optical detection signal amplifier 34 after the current-voltage conversion and is supplied to the arithmetic processing unit 36 after noise has been removed by the photo-plethysmographic signal filter unit 35.

The arithmetic processing unit 36 executes the time sharing process in accordance with the first and second pulse control signals to separate the optical detection signal supplied from the photo-plethysmographic signal filter unit 35 so as to extract the photo-plethysmographic signal corresponding to the detection light emitted from the light emitting element 8 and the photo-plethysmographic signal corresponding to the detection light emitted from the light emitting element 9. Further, the arithmetic processing unit 36 generates the biological information, such as the electrocardiogram, the heart rate, the oxygen saturation, and the pulse-wave propagation time, the acceleration plethysmogram, and the heart rate variation, based on the separated and extracted photo-plethysmographic signals and the electrocardiographic signal supplied from the differential amplifier 31. The biological information is displayed, for example, on the display screen of the display panel 5.

With the biosensor device 1 according to the first embodiment of the present invention, as described above, since the light transmissive electrocardiographic electrode 19 for obtaining the electrocardiographic signal is arranged in vertically overlapped relation to the light emitting elements 8 and 9 and the light receiving element 10 for obtaining the photo-plethysmographic signal, the size of the biosensor device 1 can be reduced while the size of the light transmissive electrocardiographic electrode 19 is set to be sufficiently large and the distance between each of the light emitting elements 8 and 9 and the light receiving element 10 is set to be sufficiently long.

Also, since the size of the light transmissive electrocardiographic electrode 19 can be set sufficiently large while the size reduction of the biosensor device 1 is realized, more stable contact between the user's thumb and the light transmissive electrocardiographic electrode 19 can be ensured, and the SN ratio of the electrocardiographic signal can be increased.

Further, since the distance between each of the light emitting elements 8 and 9 and the light receiving element 10 is set to be sufficiently long while the size reduction of the biosensor device 1 is realized, the SN ratio of the photo-plethysmographic signal can also be increased. In more detail, by setting the distance between each of the light emitting elements 8 and 9 and the light receiving element 10 to be sufficiently long, a ratio of the reflected light having passed through the artery under the skin of the user's thumb to the reflected light having been reflected at the outer surface of the skin of the user's thumb can be relatively increased in the reflected light received by the light receiving element 10. As a result, a ratio of the AC signal component useful as the photo-plethysmographic signal to the DC signal component not useful as the photo-plethysmographic signal can be relatively increased in the optical detection signal corresponding to the reflected light that is received by the light receiving element 10. Hence, the SN ratio of the photo-plethysmographic signal can be increased.

Moreover, since the light emitting elements 8 and 9 and the light receiving element 10 are arranged under the light transmissive electrocardiographic electrode 19, there is no need of forming, in the electrode surface, the recesses or the holes for mounting the light emitting elements and the light receiving element unlike the related art. Therefore, the respective surfaces of the electrocardiographic electrodes 19 and 24 can be formed flat and more stable contact can be ensured between the user's finger and each of the electrocardiographic electrodes 19 and 24. As a result, the SN ratio of the electrocardiographic signal can be increased.

Also, the light transmissive electrocardiographic electrode 19 and the light transmissive insulating film 20, which are arranged above the light emitting elements 8 and 9 and the light receiving element 10, can be utilized as covers for protecting the light emitting elements 8 and 9 and the light receiving element 10. Accordingly, the light emitting elements 8 and 9 and the light receiving element 10 can be protected against externally applied friction and shocks.

Since the two light emitting elements 8 and 9 emitting the detection lights in the different wavelength ranges are provided, the oxygen saturation of the living body can be measured.

In addition, the peripheral wall reflectors 16 are defined by the solder fillets that are formed when mounting, onto the base plate 7, the surface-mounted components 11, 12, 13 and 17, which are arranged around the light emitting elements 8 and 9 and the light receiving element 10, and the peripheral wall reflectors 16 reflect not only the detection lights emitted from the light emitting elements 8 and 9, but also the reflected lights after the detection lights have been reflected. Therefore, the detection lights can be collected toward the user's finger contacted with the contact surface 20A of the light transmissive insulating film 20, and the reflected lights of the detection lights can be collected toward the light receiving element 10. As a result, the SN ratio of the photo-plethysmographic signal obtained from the user's finger can be increased.

The above-described light collecting effect can be realized without separately adding other components dedicated for forming the peripheral wall reflectors 16. Hence, the size of the biosensor device 1 can be reduced and the manufacturing cost of the biosensor device 1 can also be reduced.

Since the surface-mounted components 11, 12 and 13 arranged around the light emitting elements 8 and 9 are prepared as surface-mounted components constituting the light emitting element drive circuit 14 that drives the light emitting elements 8 and 9 and that controls the light emissions from the light emitting elements 8 and 9, the intensities of the detection lights emitted from the light emitting elements 8 and 9 can be stabilized, and the SN ratio of the photo-plethysmographic signal obtained from the user's finger can be increased.

In more detail, if the surface-mounted components 11, 12 and 13 arranged around the light emitting elements 8 and 9 include surface-mounted components constituting other electrical circuits than the drive circuit, there is a risk that noises are superimposed on, e.g., signals for driving the light emitting elements 8 and 9, and that the intensities of the detection lights emitted from the light emitting elements 8 and 9 become unstable due to the noises. In contrast, by providing the surface-mounted components arranged around the light emitting elements 8 and 9 as the surface-mounted components 11, 12 and 13 constituting the light emitting element drive circuit, it is possible to prevent noises from being superimposed on, e.g., the signals for driving the light emitting elements 8 and 9, and to stabilize the intensities of the detection lights emitted from the light emitting elements 8 and 9.

Since the insulating films 20 and 25 are formed respectively on the electrocardiographic electrodes 19 and 24, the electrocardiographic electrodes 19 and 24 can be kept from being contacted with the living body, e.g., the human finger, and further kept from being exposed to open air. Thus, moisture, etc. can be prevented from adhering to the electrocardiographic electrodes 19 and 24. Consequently, deterioration of the electrocardiographic electrodes 19 and 24 can be avoided and durability of the biosensor device 1 can be enhanced.

A second embodiment of the biosensor device according to the present invention will be described below with reference to FIG. 10. Be it noted that the same components in FIG. 10 as those of the biosensor device 1, illustrated in FIG. 4, according to the first embodiment are denoted by the same symbols and description of those components is omitted.

In the above-described biosensor device 1 according to the first embodiment, as illustrated in FIG. 4, the light transmissive electrocardiographic electrode 19 and the electrocardiographic signal filter unit 28 of the processing circuit 26 are electrically connected by the current carrying line 21 that is disposed to extend between the forward-side end surface of the light transmissive sealing member 18 and the forward-side inner peripheral surface of the light passing opening 4B.

Figure 10:
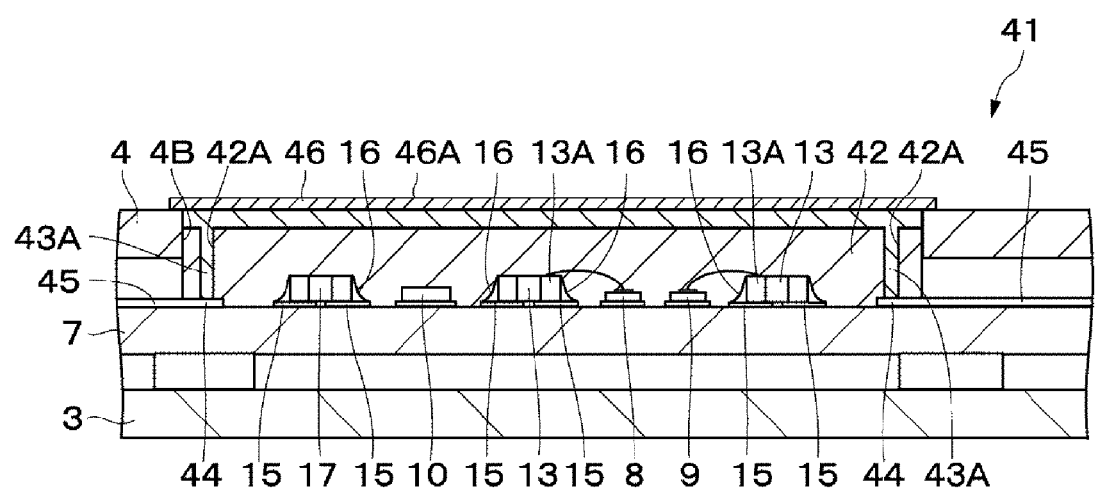
FIG. 10 is a longitudinal sectional view illustrating a light transmissive electrocardiographic electrode, a light transmissive insulating film, a base plate, a light emitting element, a light receiving element, surface-mounted components, etc. in a biosensor device according to a second embodiment.

In contrast, in the biosensor device 41 according to the second embodiment, as illustrated in FIG. 10, a light transmissive electrocardiographic electrode 43 disposed on a light transmissive sealing member 42 and an electrode pad 44 disposed on the base plate 7 are electrically connected by filling an electroconductive resin (e.g., a transparent electroconductive resin), which has optical transparency in the wavelength ranges of the lights emitted from the light emitting elements 8 and 9, in a through-hole 42A formed in the light transmissive sealing member 42. Further, the electrode pad 44 is electrically connected to the electrocardiographic signal filter unit 28 through a wiring pattern 45 on the base plate 7.

In more detail, the through-hole 42A or a through-groove, having a circular, elliptical or rectangular horizontally cross-sectional shape, is formed by dicing, laser processing, photolithography, or patterning with printing, for example, in the light transmissive sealing member 42, which is made of an insulating resin (e.g., a transparent insulating resin) having optical transparency in the wavelength ranges of the lights emitted from the light emitting elements 8 and 9, and which seals off the light emitting elements 8 and 9, the light receiving element 10, the surface-mounted components 11, 12 and 13, etc. on the base plate 7. Further, the electrode pad 44 is disposed on the base plate 7 in its region corresponding to an opening at a lower end of the through-hole 42A, and the electrode pad 44 is connected to the electrocardiographic signal filter unit 28 through the wiring pattern 45 on the base plate 7.

An electroconductive resin (e.g., a transparent electroconductive resin), which has optical transparency in the wavelength ranges of the lights emitted from the light emitting elements 8 and 9, is coated over an upper surface of the light transmissive sealing member 42, thereby forming a thin film of the electroconductive resin. At that time, part of the electroconductive resin is caused to flow into the through-hole 42A such that the thin film of the electroconductive resin formed on the upper surface of the light transmissive sealing member 42 and the electrode pad 44 on the base plate 7 are electrically connected by the electroconductive resin having flown into the through-hole 42A. The coated electroconductive resin is then cured. As a result, the light transmissive electrocardiographic electrode 43 is formed on the light transmissive sealing member 42, and an electroconductive connecting portion 43A for electrically connecting the light transmissive electrocardiographic electrode 43 and the electrode pad 44 to each other is formed in the through-hole 42A. Thereafter, a light transmissive insulating film 46 is formed on an upper surface of the light transmissive electrocardiographic electrode 43.

When the thumb of the user's left hand is contacted with a contact surface 46A of the light transmissive insulating film 46, an electrical signal relating to the electrocardiographic signal is detected through capacitive coupling between the thumb and the light transmissive electrocardiographic electrode 43, and the electrical signal is supplied to the electrocardiographic signal filter unit 28 through the electroconductive connecting portion 43A, the electrode pad 44, and the wiring pattern 45.

The thus-constructed biosensor device 41 according to the second embodiment of the present invention can also provide similar advantageous effects in operation to those in the biosensor device 1 according to the first embodiment of the present invention.

A third embodiment of the present invention will be described below with reference to FIGS. 11 to 17. Be it noted that the same components in the third embodiment as those in the first embodiment are denoted by the same symbols and description of those components is omitted.

Figure 11:
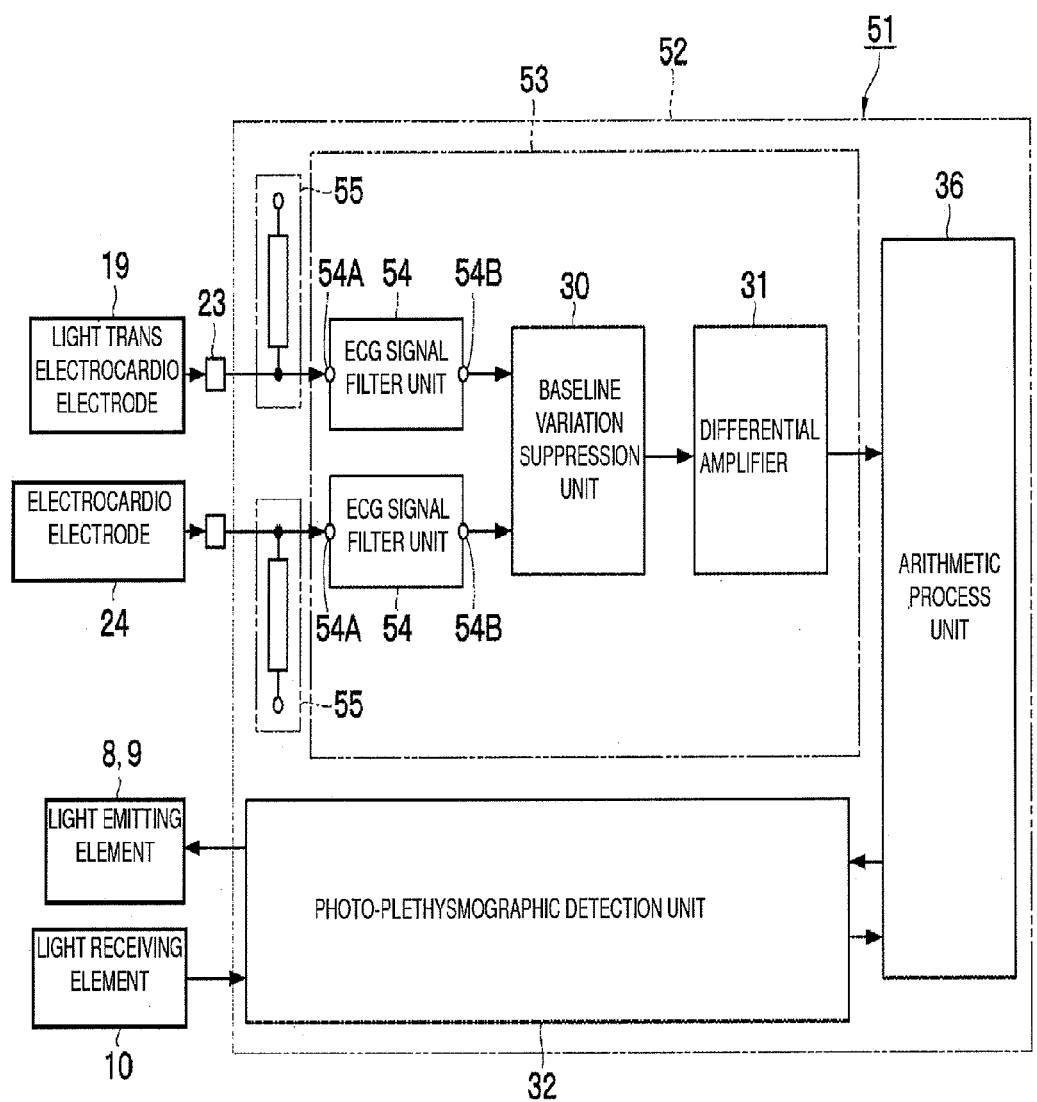
FIG. 11 is a block diagram illustrating the electrical configuration of a biosensor device according to a third embodiment.

As illustrated in FIG. 11, a biosensor device 51 according to the third embodiment of the present invention includes a processing circuit 52. The processing circuit 52 primarily includes, similarly to the processing circuit 26 in the first embodiment, an electrocardiographic signal detection unit 53, the photo-plethysmographic signal detection unit 32, and the arithmetic processing unit 36. The electrocardiographic signal detection unit 53 includes, similarly to the electrocardiographic signal detection unit 27 in the first embodiment, two electrocardiographic signal filter units 54 (described below), the baseline variation suppression unit 30, and the differential amplifier 31.

The electrocardiographic signal filter units 54 are disposed in the input terminal side of the processing circuit 52, and their input terminals 54A serve as input terminals of the electrocardiographic signal detection unit 53. In more detail, the input terminals 54A of the electrocardiographic signal filter units 54 are connected respectively to the electrocardiographic electrode 19 and 24, and output terminals 54B of the electrocardiographic signal filter units 54 are connected respectively to the input terminals of the differential amplifier 31 through the baseline variation suppression unit 30. The electrocardiographic signal filter units 54 reduce noises included in the electrical signals relating to the electrocardiographic signal, which are detected through capacitive coupling between the human thumbs and the electrocardiographic electrodes 19 and 24 when the human thumbs are brought into contact with the contact surfaces 20A and 25A of the insulating films 20 and 25 on the electrocardiographic electrodes 19 and 24.

Figure 12:
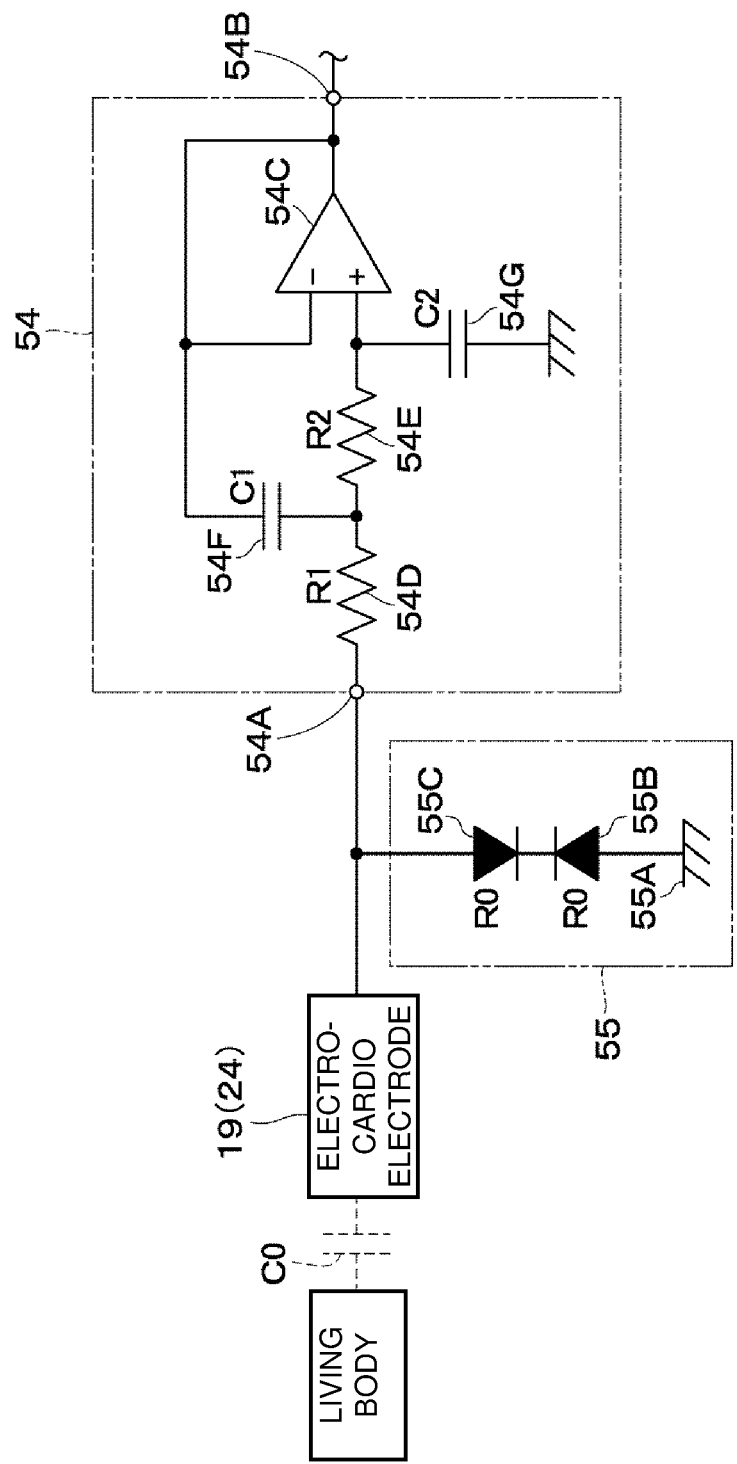
FIG. 12 is a circuit diagram illustrating an electrocardiographic signal filter unit, a clamp circuit, etc.

The electrocardiographic signal filter units 54 are each constituted by, e.g., a low-pass filter. In more detail, as illustrated in FIG. 12, the electrocardiographic signal filter units 54 are each constituted, for example, by a Sallen-Key circuit including an operational amplifier 54C, first and second resistances 54D and 54E connected in series between a non-inverting terminal of the operational amplifier 54C and the input terminal 54A, a first capacitor 54F connected between a junction between the first and second resistances 54D, 54E and an output terminal of the operational amplifier 54C, and a second capacitor 54G connected between the non-inverting terminal of the operational amplifier 54C and a ground. An inverting terminal and the output terminal of the operational amplifier 93C are connected to each other. In such a configuration, the cutoff frequency of the electrocardiographic signal filter unit 54 is determined depending on resistance values R1 and R2 of the resistances 54D and 54E and capacity values C1 and C2 of the capacitors 54F and 54G.

A clamp circuit 55 is connected to the input terminal 54A of the electrocardiographic signal filter unit 54. The clamp circuit 55 includes a ground 55A serving as a DC constant-voltage source, and diodes 55B and 55C each connected between the ground 55A and the input terminal 54A and serving as a high-impedance element. In such a configuration, the diodes 55B and 55C are connected in series in a mutually confronting state such that forward directions of the diodes are opposed to each other. Thus, cathodes of the diodes 55B and 55C are connected to each other, an anode of the diode 55B is connected to the ground 55A, and an anode of the diode 55C is connected to the input terminal 54A.

Therefore, the diode 55B has a reverse characteristic for an electrical signal at a voltage higher than the ground voltage and serves as a high-impedance element having a resistance value R0 of, e.g., 100 MΩ or more. On the other hand, the diode 55C has a reverse characteristic for an electrical signal at a voltage lower than the ground voltage and serves as a high-impedance element having a resistance value R0 of, e.g., 100 MΩ or more. The clamp circuit 55 fixedly holds a reference potential at the input terminal 54A, i.e., at the connected end of the clamp circuit 55, to be constant as the ground voltage.

Herein, the impedance when looking at the electrocardiographic signal detection unit 53 including the differential amplifier 31 from the connected end of the clamp circuit 55 is set to a value larger than the impedance (resistance value R0) of the clamp circuit 55. In more detail, the impedance of the clamp circuit 55 is primarily determined by the resistance value R0 in the reverse characteristics of the diodes 55B and 55C. Also, the resistance value R0 is generally set to a value smaller than 1 GΩ or more that is the input impedance at the non-inverting terminal (input terminal) of the operational amplifier 54C in the electrocardiographic signal filter unit 54. Accordingly, the impedance when looking at the electrocardiographic signal detection unit 53 from the electrocardiographic electrodes 19 and 24 is determined by the resistance value R0 of the diodes 55B and 55C.

In view of the above point, the resistance value R0 of the diodes 55B and 55C will be discussed below. When the electrical signals relating to the electrocardiographic signal are measured through capacitive coupling between the living body and the electrocardiographic electrodes 19, 24 as in the biosensor device 51, a loss caused at the input terminal 54A of each electrocardiographic signal filter circuit 54 depends on an electrostatic capacity value C0 between the living body and each of the electrocardiographic electrodes 19, 24 and the resistance value R0 of the clamp circuit 55. Therefore, unless the electrostatic capacity value C0 and the resistance value R0 are appropriately selected, a loss is caused in a frequency band of the electrocardiographic signal.

In this embodiment, each of the electrocardiographic electrodes 19 and 24 has a size comparable to that of a finger tip, i.e., a contact portion of the living body. Accordingly, the electrocardiographic electrodes 19 and 24 are each in a rectangular shape with one side having a length of about 10 mm to 30 mm or an elliptic shape with a diameter of about 10 mm to 30 mm. Further, the electrocardiographic electrodes 19 and 24 are covered respectively with the insulating films 20 and 25 each having a thickness of about several μm to several tens μm. Hence, the electrostatic capacity value C0 generated between the living body and each of the electrocardiographic electrodes 19, 24 is about 70 pF to 600 pF.

In order to enable the electrical signal relating to the electrocardiographic signal to be detected with respect to the electrostatic capacity value C0, it is required to reduce distortion of the waveform of the electrical signal and to reduce the influence of radiation noise. Those requirements are satisfied when the resistance value R0 is larger than a value indicated by a boundary line X in FIG. 13. In other words, those requirements are satisfied when the resistance value R0 falls within a region B in FIG. 13.

Figure 13:
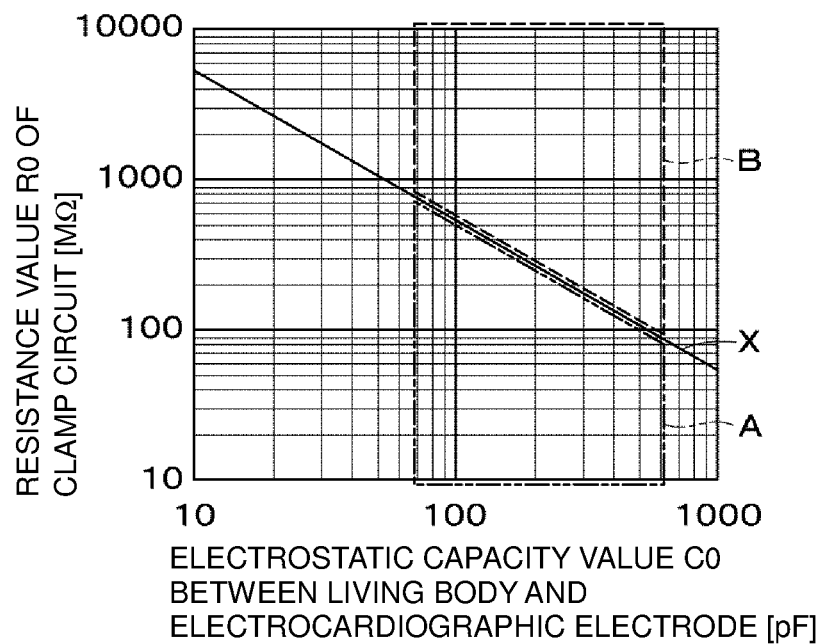
FIG. 13 is a graph to explain the relationship of an electrostatic capacity value between a living body and the electrocardiographic electrode versus a resistance value of the clamp circuit.
Figure 14:
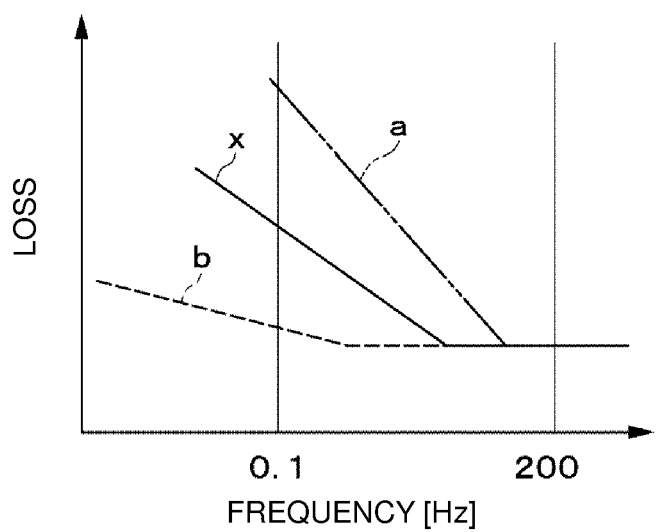
FIG. 14 is a frequency characteristic graph plotting the relationship between a signal loss in an input portion of an electrocardiographic signal detection unit and a frequency of an electrical signal relating to the electrocardiographic signal.
Figure 15:
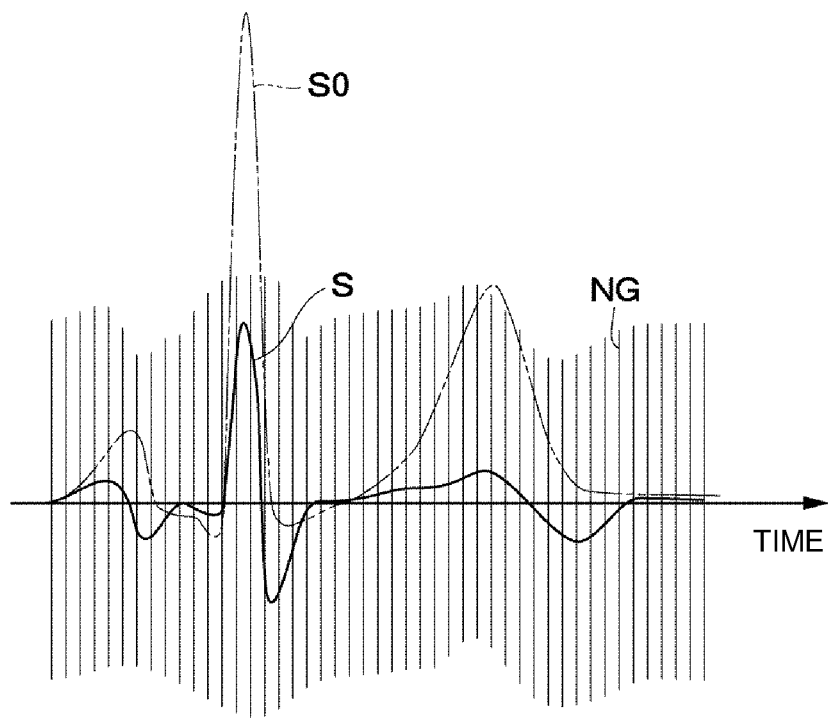
FIG. 15 is a characteristic line chart indicating changes over time of the electrical signal relating to the electrocardiographic signal and radiation noise when the resistance value of the clamp circuit is within a region A in FIG. 13.

More specifically, when the resistance value R0 falls within a region A in FIG. 13, the loss in a frequency band of 0.1 to 200 Hz of the electrocardiographic signal is increased as represented by a characteristic line a in FIG. 14. In that case, as illustrated in FIG. 15, distortion of an electrical signal S relating to the electrocardiographic signal is increased in comparison with an ideal electrical signal S0 relating to the electrocardiographic signal having no loss, and an appropriate electrical signal cannot be detected.

Figure 16:
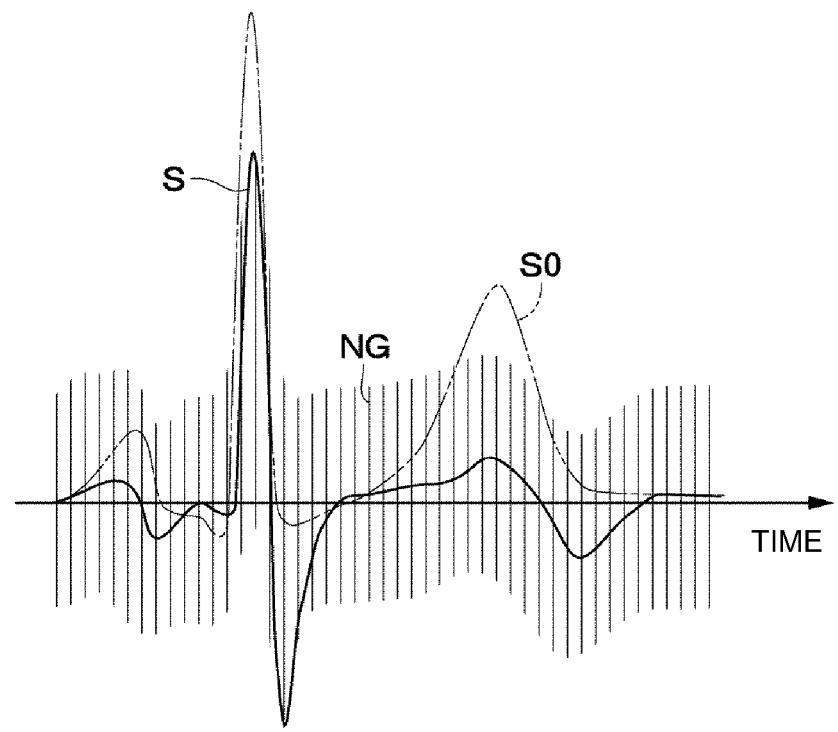
FIG. 16 is a characteristic line chart indicating changes over time of the electrical signal relating to the electrocardiographic signal and radiation noise when the resistance value of the clamp circuit is near a boundary line X in FIG. 13.

On the other hand, when the resistance value R0 is near the boundary line X in FIG. 13, the loss in the frequency band of 0.1 to 200 Hz of the electrocardiographic signal is reduced as represented by a characteristic line x in FIG. 14. In that case, as illustrated in FIG. 16, the distortion of the electrical signal S relating to the electrocardiographic signal is reduced and the waveform of the electrical signal S comes closer to that of the ideal electrical signal S0. Further, since the resistance value R0 is larger than that in the region A, the influence of radiation noise NG is reduced. Accordingly, it is difficult to detect the detailed waveform of the electrical signal relating to the electrocardiographic signal, but a peak of the electrocardiographic signal can be detected.

Figure 17:
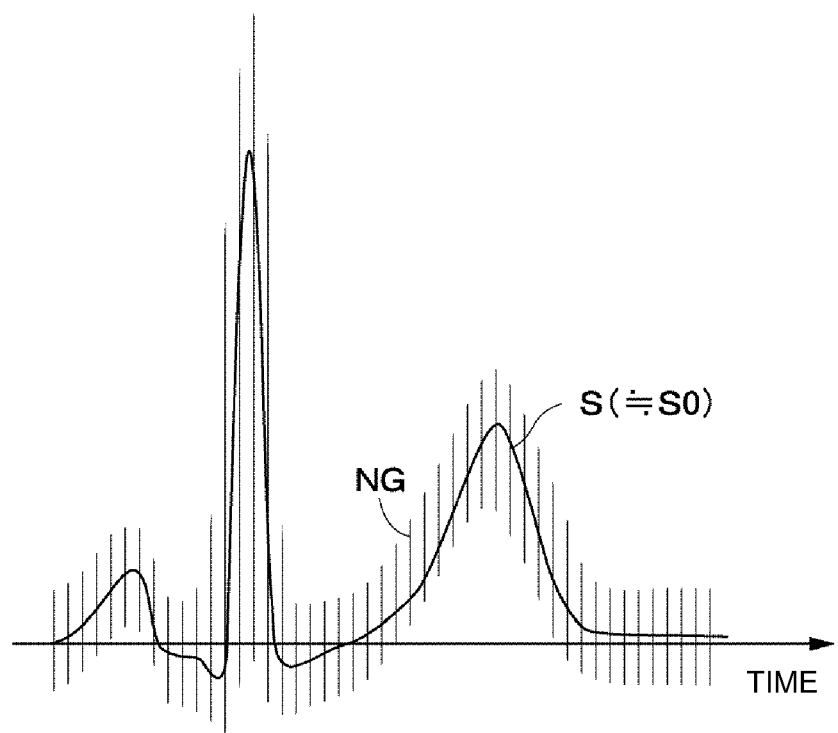
FIG. 17 is a characteristic line chart indicating changes over time of the electrical signal relating to the electrocardiographic signal and radiation noise when the resistance value of the clamp circuit is within a region B in FIG. 13.

When the resistance value R0 falls within the region B in FIG. 13, the loss in the frequency band of 0.1 to 200 Hz of the electrocardiographic signal is further reduced as represented by a characteristic line b in FIG. 14. In that case, as illustrated in FIG. 17, the waveform of the electrical signal S relating to the electrocardiographic signal is changed substantially in the same manner as that of the ideal electrical signal S0, and the distortion of the electrical signal S relating to the electrocardiographic signal and the influence of the radiation noise NG are further reduced. Consequently, the resistance value R0 needs to be held within the region B in FIG. 13 in order to reduce both the distortion of the electrical signal S and the influence of the radiation noise NG. In other words, the resistance value R0 requires to be, e.g., 100 MΩ or more.

In the case of an ordinary resistance element used in a clamp circuit, a resistance value is about several MΩ at maximum and a high impedance at the above-mentioned level of 100 MΩ or more cannot be obtained. Therefore, when the ordinary resistance element is used, the distortion of the electrical signal S relating to the electrocardiographic signal is increased and the SN ratio is reduced. On the other hand, in the clamp circuit 55 according to this embodiment, the high impedance of 100 MΩ or more is realized as the resistance value R0 by utilizing the reverse characteristics of the diodes 55B and 55C.

More specifically, in this embodiment, the voltages of the electrical signals relating to the electrocardiographic signal and generated depending on the sizes of the electrocardiographic electrodes 19 and 24 are each about 1 to 2 mV. In that case, when the diodes 55B and 55C are connected to each other in oppositely faced relation as illustrated in FIG. 12, the generated voltage of 1 to 2 mV is applied as a reverse voltage to one of the diodes 55B and 55C due to the reverse characteristic thereof. However, the breakdown voltage of each of the diodes 55B and 55C is usually about 1 V. Thus, since the reverse voltage is sufficiently lower than the breakdown voltage, no electric currents flow through the diodes 55B and 55C. As a result, each of the diodes 55B and 55C functions as the high-impedance element of, e.g., 100 MΩ or more. In this embodiment, therefore, the electrical signal S relating to the electrocardiographic signal can be detected as a satisfactory signal having smaller distortion and a higher SN ratio.

The externally mixed radiation noise NG primarily includes noise (50 Hz or 60 Hz) from a commercial power supply and higher harmonics (i.e., at integer multiples of 50 Hz or 60 Hz) thereof. The noise from the commercial power supply is applied to the two electrocardiographic electrodes 19 and 24 in the same phase, and hence the noises detected through the two electrocardiographic electrodes 19 and 24 are canceled off by the differential amplifier 31. The other noises of 200 Hz or higher are removed by the electrocardiographic signal filter units 54. Accordingly, the cutoff frequency of each of the electrocardiographic signal filter units 54 is set to an appropriate value of 200 Hz or higher.

The thus-constructed third embodiment of the present invention can provide substantially the same advantageous effects as those in the above-described first embodiment. In trying to detect the electrical signal relating to the electrocardiographic signal through the capacitive coupling between each of the electrocardiographic electrodes 19, 24 and the living body, if the input impedance when looking at the electrocardiographic signal detection unit 53 from the electrocardiographic electrodes 19 and 24 is low, the loss in the frequency band of the electrical signal relating to the electrocardiographic signal is increased and the electrocardiographic signal cannot be detected. Also, if the reference potential at the input terminal 54A of the electrocardiographic signal filter unit 54 is not fixedly held, variations in a central potential of the electrical signal relating to the electrocardiographic signal are increased and stable measurement of the electrocardiographic signal is difficult to realize. In contrast, according to the third embodiment, since the reference potential at the input terminal 54A of the electrocardiographic signal filter unit 54 can be fixedly held by the clamp circuit 55, variations in the central potential of the electrical signal relating to the electrocardiographic signal can be reduced. As a result, the SN ratio can be increased and the electrical signal relating to the electrocardiographic signal can be stably detected.

Further, since the clamp circuit 55 is constituted by the diodes 55B and 55C each serving as the high-impedance element and the impedance when looking at the input terminal of the electrocardiographic signal detection unit 53 from the connected end of the clamp circuit 55 is set to be larger than the impedance (resistance value R0) of the clamp circuit 55, the loss in the frequency band of the electrical signal relating to the electrocardiographic signal can be reduced.

A fourth embodiment of the present invention will be described below with reference to FIGS. 18 and 19. Be it noted that the same components in the fourth embodiment as those in the first embodiment are denoted by the same symbols and description of those components is omitted.

Figure 18:
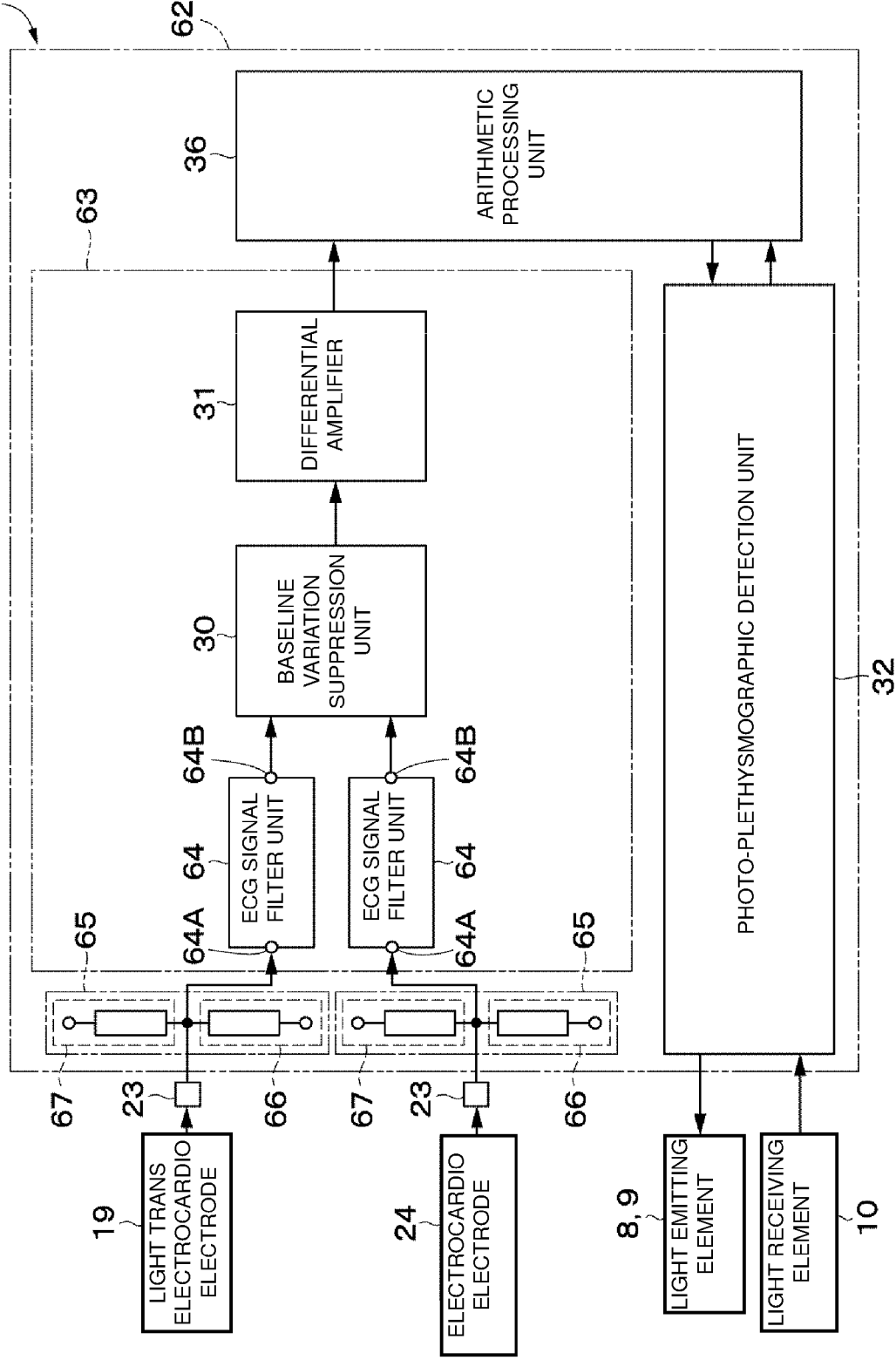
FIG. 18 is a block diagram illustrating the electrical configuration of a biosensor device according to a fourth embodiment.
Figure 19:
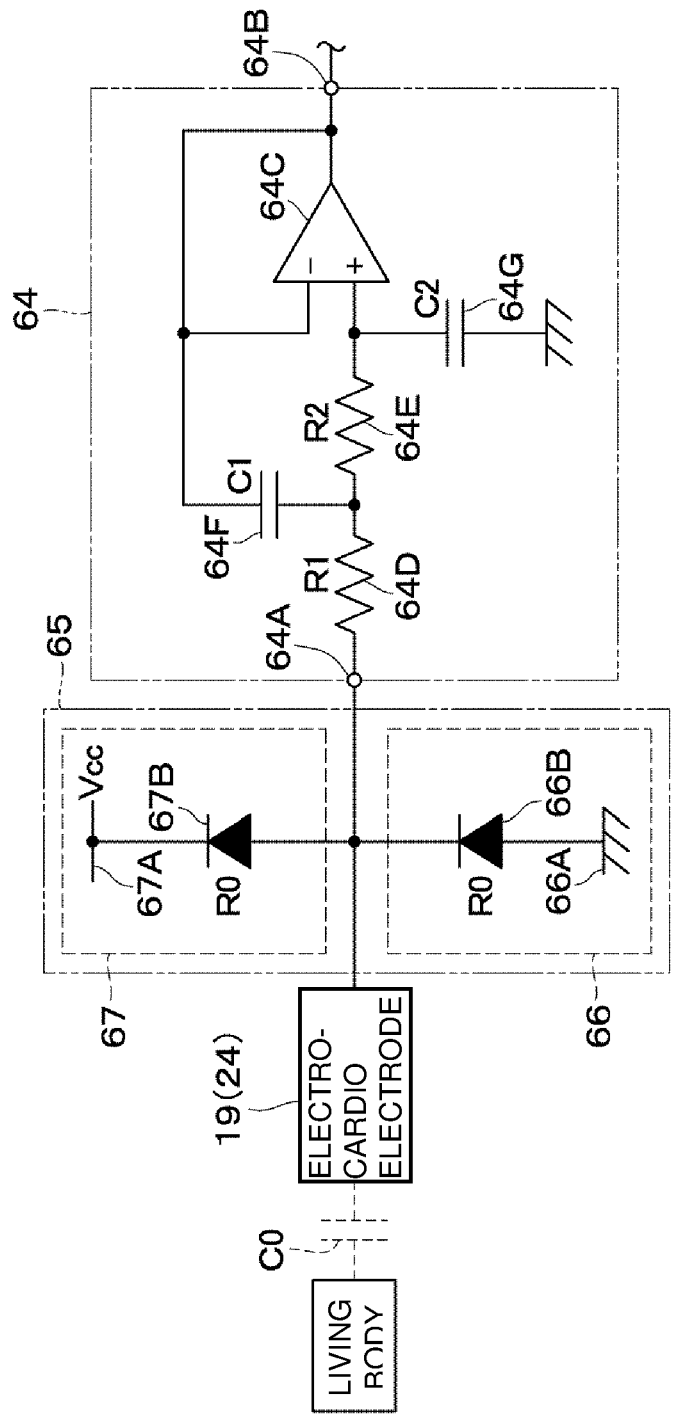
FIG. 19 is a circuit diagram illustrating an electrocardiographic signal filter unit, a clamp circuit, etc.

As illustrated in FIG. 18, a biosensor device 61 according to the fourth embodiment of the present invention includes a processing circuit 62. As in the processing circuit 26 in the first embodiment, the processing circuit 62 primarily includes an electrocardiographic signal detection unit 63, the photoplethysmographic signal detection unit 32, and the arithmetic processing unit 36. As in the electrocardiographic signal detection unit 27 in the first embodiment, the electrocardiographic signal detection unit 63 includes two electrocardiographic signal filter units 64 (described below), the baseline variation suppression unit 30, and the differential amplifier 31.

Input terminals 64A of the electrocardiographic signal filter units 64 serve as input terminals of the electrocardiographic signal detection unit 63 and are connected respectively to the electrocardiographic electrodes 19 and 24. Output terminals 64B of the electrocardiographic signal filter units 64 are connected respectively to the input terminals of the differential amplifier 31 through the baseline variation suppression unit 30. Almost like the electrocardiographic signal filter units 54 in the third embodiment, the electrocardiographic signal filter units 64 are each, for example, in the form of a low-pass filter that is constituted by a Sallen-Key circuit including an operational amplifier 64C, first and second resistances 64D and 64E, and first and second capacitors 64F and 64G. The electrocardiographic signal filter units 64 are disposed in the input terminal side of the processing circuit 62, and they reduce noises in the electrical signals relating to the electrocardiographic signal.

A clamp circuit unit 65 is connected to the input terminal 64A of each of the electrocardiographic signal filter units 64. The clamp circuit unit 65 includes two first and second clamp circuits 66 and 67.

The first clamp circuit 66 includes a ground 66A serving as a first DC constant-voltage source, and a diode 66B connected between the ground 66A and the input terminal 64A and serving as a first high-impedance element. In such a configuration, an anode of the diode 66B is connected to the ground 66A, and a cathode of the diode 66B is connected to the input terminal 64A. Therefore, the diode 66B has a reverse characteristic for an electrical signal at a voltage higher than the ground voltage and serves as a high-impedance element having a resistance value R0 of, e.g., 100 MΩ or more.

On the other hand, the second clamp circuit 67 includes, e.g., a drive voltage source 67A for the operational amplifier 64C, which serves as a second DC constant-voltage source, and a diode 67B connected between the drive voltage source 67A and the input terminal 64A and serving as a second high-impedance element. In such a configuration, an anode of the diode 67B is connected to the input terminal 64A, and a cathode of the diode 67B is connected to the drive voltage source 67A. Therefore, the diode 67B has a reverse characteristic for an electrical signal at a voltage lower than a drive voltage Vcc provided by the drive voltage source 67A and serves as a high-impedance element having a resistance value R0 of, e.g., 100 MΩ or more.

Herein, the impedance when looking at the electrocardiographic signal detection unit 63 from connected ends of the clamp circuits 66 and 67 is set to a value larger than the impedance (resistance value R0) of the clamp circuits 66 and 67. In more detail, the resistance value R0 in the reverse characteristics of the diodes 66B and 67B, which defines the impedance of each of the clamp circuits 66 and 67, is set to a value smaller than 1 GΩ or more that is the input impedance at a non-inverting terminal (input terminal) of the operational amplifier 64C in the electrocardiographic signal filter units 64.

The clamp circuits 66 and 67 fixedly hold a reference potential at the input terminal 64A, i.e., at the connected ends of the clamp circuits 66 and 67, to a constant voltage that is determined in advance to a value between the drive voltage Vcc and the ground voltage.

The thus-constructed fourth embodiment of the present invention can provide substantially the same advantageous effects as those in the above-described first and third embodiments. In particular, with the fourth embodiment, since the plural clamp circuits 66 and 67 are connected to the input terminal 64A of the electrocardiographic signal filter unit 64, the reference potential at the input terminal 64A of the electrocardiographic signal filter unit 64 can be set to any desired value between the ground voltage in the first clamp circuit 66 and the drive voltage Vcc in the second clamp circuit 67. Consequently, the reference potential at the input terminal 64A of the electrocardiographic signal filter unit 64 can be set to an appropriate value in consideration of an amplifiable range of the operational amplifier 64C in the electrocardiographic signal filter unit 64, the magnitude of the electrical signal relating to the electrocardiographic signal, and so on.

Figure 20:
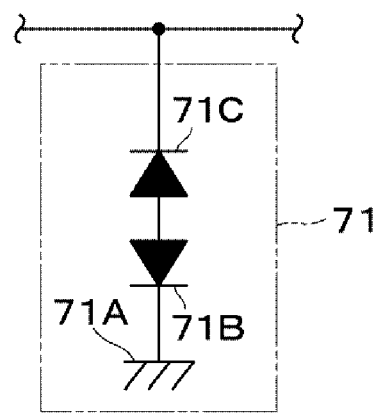
FIG. 20 is a circuit diagram illustrating a clamp circuit according to a fifth embodiment.

In the above-described clamp circuit 55 according to the third embodiment, the two diodes 55B and 55C are arranged with their cathodes connected to each other. However, the present invention is not limited to such an arrangement. For example, as in a clamp circuit 71 according to a fifth embodiment illustrated in FIG. 20, two diodes 71B and 71C connected to a ground 71A may be arranged with their anodes connected to each other. Alternatively, a set of the diodes 55B and 55C or the diodes 71B and 71C oppositely faced to each other may be connected plural in series. Those arrangements of the diodes 55B and 55C according to the third embodiment and the diodes 71B and 71C according to the fifth embodiment can also be applied to the diodes 66B and 67B (high-impedance elements) of the clamp circuits 66 and 67 according to the fourth embodiment.

Figure 21:
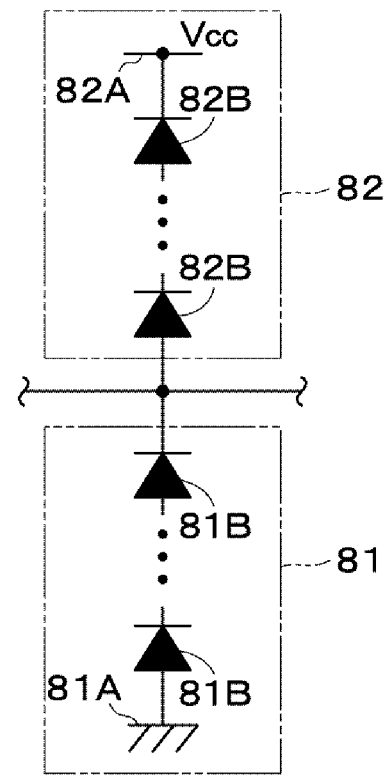
FIG. 21 is a circuit diagram illustrating a clamp circuit according to a sixth embodiment.

In the above-described clamp circuits 66 and 67 according to the fourth embodiment, the high-impedance element is constituted by the single diode 66B or 67B. However, the present invention is not limited to such a configuration. For example, as in clamp circuits 81 and 82 according to a sixth embodiment illustrated in FIG. 21, plural diodes 81B and plural diodes 82B may be connected in series to a ground 81A and a drive voltage source 82A, respectively, in such a way that forward directions of those diodes are oriented in the same direction. In that case, respective adjacent two of the diodes 81B and the diodes 82B are interconnected with a cathode of one and an anode of the other connected to each other. Such an arrangement can reduce reverse currents flowing through the diodes 81B and the diodes 82B, and can easily increase the resistance values of the clamp circuits 81 and 82.

In the third to sixth embodiments, the diodes 55B, 55C, 66B, 67B, 71B, 71C, 81B and 82B are employed as the high-impedance elements. Instead of the diodes 55B, 55C, 66B, 67B, 71B, 71C, 81B and 82B, however, bipolar transistors may be employed, for example, in the form that a base and a collector of each bipolar transistor are short-circuited so as to utilize a base-emitter characteristic. Alternatively, a gate and a source of a field effect transistor may be short-circuited so as to utilize a gate-source characteristic.

As another example, a high-resistance element, a high-resistance semiconductor film, or the like may also be used as the high-impedance element. The high-resistance semiconductor film can be formed by any of such processes as sputtering, CVD, MBE, and vacuum deposition. However, some other suitable film forming method may be used instead. One example of the high-resistance semiconductor film is an oxide semiconductor film, but another type of high-resistance semiconductor film can also be used. Further, the high-impedance element may be obtained by forming an insulator substrate made of, e.g., silicon, gallium or arsenic, and by reducing the resistance of the substrate. The resistance of the substrate can be reduced, for example, by adding impurities to the substrate with, e.g., thermal diffusion or ion implanting.

In the above-described fourth embodiment, the same first and second clamp circuits 66 and 67 (i.e., the same clamp circuit unit 65) are connected to each of the electrocardiographic electrodes 19 and 24. However, the present invention is not limited to such an arrangement. For example, different clamp circuit units may be connected to the two electrocardiographic electrodes, respectively. In that case, a first DC constant-voltage source of a first clamp circuit connected to one of the electrocardiographic electrodes and a first DC constant-voltage source of a first clamp circuit connected to the other electrocardiographic electrode may have different potentials from each other. Similarly, a second DC constant-voltage source of a second clamp circuit connected to the one electrocardiographic electrode and a second DC constant-voltage source of a second clamp circuit connected to the other electrocardiographic electrode may have different potentials from each other. Further, respective resistance values R0 of the diodes 66B and 67B in the clamp circuits 66 and 67 may differ from each other.

While, in the third and fourth embodiments, the electrocardiographic signal filter units 54 and 64 for removing the radiation noises are constituted as active filters including operational amplifiers 54C and 64C each having the high input impedance, the filter units may be each constituted as a passive filter not including the operational amplifier.

In the above-described third or fourth embodiment, the electrocardiographic signal filter unit 54 or 64, which constitutes the amplification circuit unit, and the clamp circuit 55 or the clamp circuits 66 and 67 are connected to each of the electrocardiographic electrodes 19 and 24 in the first embodiment. However, the present invention is not limited to such an arrangement. For example, the amplification circuit unit and the clamp circuit(s) may be connected to the electrocardiographic electrode 43 in the second embodiment.

A seventh embodiment of the present invention will be described below with reference to FIGS. 22 and 23. Be it noted that the same components in the seventh embodiment as those in the first embodiment are denoted by the same symbols and description of those components is omitted.

Figure 22:
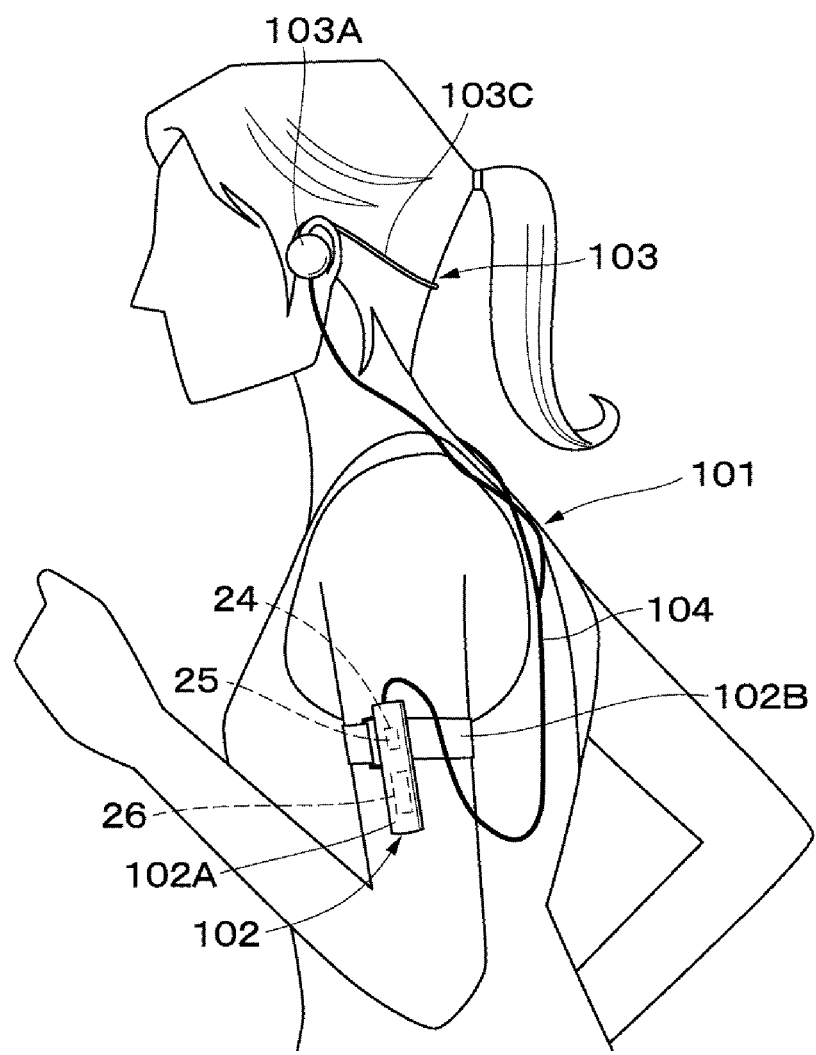
FIG. 22 is an explanatory view illustrating a state where a user wears a biosensor device according to a seventh embodiment.
Figure 23:
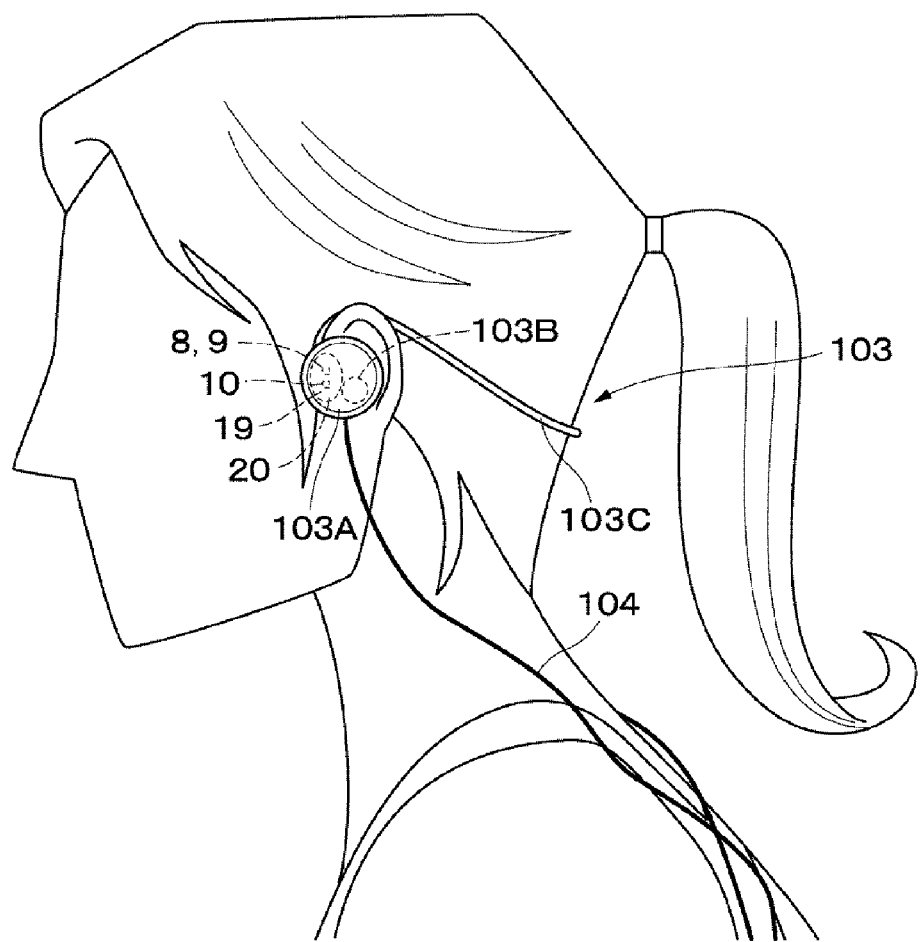
FIG. 23 is an explanatory view illustrating, in an enlarged scale, the surroundings of a headphone in FIG. 22.

In a biosensor device 101 according to the seventh embodiment of the present invention, as illustrated in FIG. 22, the processing circuit 26 is contained inside a casing 102A, i.e., a first housing, of a portable device 102, such as a portable music player or a cellular phone. The casing 102A is attached to, e.g., a user's arm by using a fixing band 102B. In addition to the processing circuit 26, the electrocardiographic electrode 24 is also contained in the casing 102A. Further, the insulating film 25 coated over the electrocardiographic electrode 24 is exposed at the surface of the casing 102A in a position opposing to the electrocardiographic electrode 24 such that the insulating film 25 serves as a first portion to be contact with the user's skin, e.g., the surface of the user's arm. Moreover, the casing 102A has the function such as that of a portable music player for outputting music, voices, etc. from a headphone 103.

On the other hand, the light transmissive electrocardiographic electrode 19, the light emitting elements 8 and 9, and the light receiving element 10 are mounted to the headphone 103 that is provided separately from the casing 102A. The headphone 103 includes speaker casings 103A (only one thereof illustrated) which can be attached to both ears, and each of the speaker casings 103A constitutes a second housing. The speaker casings 103A include ear chips 103B with speakers, etc. built therein, and they are connected to each other by a head band 103C such that the speaker casings 103A lightly grip the user's head from both sides with resiliency of the head band 103C.

The light transmissive electrocardiographic electrode 19, the light emitting elements 8 and 9, and the light receiving element 10 are contained in one of the speaker casings 103A of the headphone 103, which one is attached to one ear of the user. More specifically, the light transmissive electrocardiographic electrode 19, the light emitting elements 8 and 9, and the light receiving element 10 are arranged on the speaker casing 103A at a position corresponding to, e.g., a front portion of the user's earlobe. Further, the light transmissive insulating film 20 coated over the light transmissive electrocardiographic electrode 19 is exposed at the surface of the speaker casings 103A in a position opposing to the light transmissive electrocardiographic electrode 19 such that the light transmissive insulating film 20 serves as a second portion to be contact with the user's skin, e.g., the front portion of the user's earlobe. Additionally, an area of the light transmissive electrocardiographic electrode 19 is set substantially the same as that of the electrocardiographic electrode 24.

The light transmissive electrocardiographic electrode 19, etc. are electrically connected to the processing circuit 26 in the casing 102A through a cable 104 that is led out from the casing 102A. The cable 104 is desirably constituted by a coaxial line or a twisted pair wire, for example, in order to reduce the influence of radiation noises from the ambient environment and the headphone 103. Further, the cable 104 is desirably integrated with a cable connecting the headphone 103 and the portable music player, for example.

The thus-constructed seventh embodiment of the present invention can provide substantially the same advantageous effects as those in the above-described first embodiment. When the electrocardiographic signal is measured in a state that the fingers of both the hands are contacted with the electrocardiographic electrodes 19 and 24 as in the first embodiment, the posture of the user is fixed and hence it is difficult to continuously perform the measurement for a long time. In addition, there is a problem that the user is inevitably conscious of the measurement and changes of the living body in an unconscious condition cannot be measured.

In contrast, in the seventh embodiment, the processing circuit 26 is contained in the casing 102A having the function such as that of the portable music player, and the light transmissive electrocardiographic electrode 19 is disposed in the headphone 103, the headphone 103 being electrically connected to the casing 102A through the cable 104. Therefore, the user can make the electrocardiographic measurement while listening, e.g., music. As a result, the user can continuously measure the electrocardiographic signal, for example, without needing any dedicated measurement device and without being aware of the measurement. Moreover, since the electrocardiographic signal is measured between the ear and the arm, the voltage of the electrocardiographic signal is relatively increased and higher durability is ensured against radiation noises from the ambient environment and noises caused by body motions. Hence, the continuous measurement can be performed in a stable state.

Also, since the light transmissive electrocardiographic electrode 19, the light transmissive insulating film 20, the light emitting elements 8 and 9, and the light receiving element 10 are mounted to the speaker casing 103A of the headphone 103, those components undergo smaller variations in body motions during exercise than when they are attached to the arm, for example. Further, the electrical signal relating to the electrocardiographic signal and the optical detection signal relating to the photo-plethysmographic signal can be detected from the front portion of the user's earlobe where the skin is thinner than that of the arm. Accordingly, noises caused by the variations in body motions during exercise can be reduced in comparison with those caused when the above-mentioned signals are detected from, e.g., the arm. In addition, the photo-plethysmogram, the oxygen saturation, the electrocardiogram, etc. can be continuously measured at a high SN ration even during the exercise. It is hence possible to measure information relating to not only a heart rate and a heartbeat interval fluctuation, but also a blood pressure variation and a blood vessel age, which are determined from the oxygen saturation and the beat-wave propagation time. As a result, a degree of tension or excitation of the user and changes in body situation during the exercise can be accurately estimated.

Since the light emitting elements 8 and 9 and the light receiving element 10 are arranged under the light transmissive electrocardiographic electrode 19, etc. and the surface of the light transmissive electrocardiographic electrode 19, etc. is flat, sweat and dirt generated during the exercise can be prevented from being deposited on the light emitting elements 8 and 9 and the light receiving element 10. Accordingly, the measurement can be performed in a stable state, and the light emitting elements 8 and 9 and the light receiving element 10 can be protected against externally applied friction and shocks.

In the seventh embodiment, the electrocardiographic electrode 24 is disposed in the casing 102A of the portable device 102, whereas the light transmissive electrocardiographic electrode 19, the light transmissive insulating film 20, the light emitting elements 8 and 9, and the light receiving element 10 are disposed in the speaker casing 103A of the headphone 103. However, the present invention is not limited to such an arrangement. For example, the electrocardiographic electrode 24 may be disposed in the speaker casing 103A, whereas the light transmissive electrocardiographic electrode 19, the light transmissive insulating film 20, the light emitting elements 8 and 9, and the light receiving element 10 may be disposed in the casing 102A. Alternatively, only the processing circuit 26 may be contained in the casing 102A. In that case, the light transmissive electrocardiographic electrode 19, the light transmissive insulating film 20, the light emitting elements 8 and 9, and the light receiving element 10 can be disposed in one of the speaker casings 103A, whereas the electrocardiographic electrode 24 can be disposed in, e.g., the other speaker casing 103A instead of the casing 102A.

Figure 24:
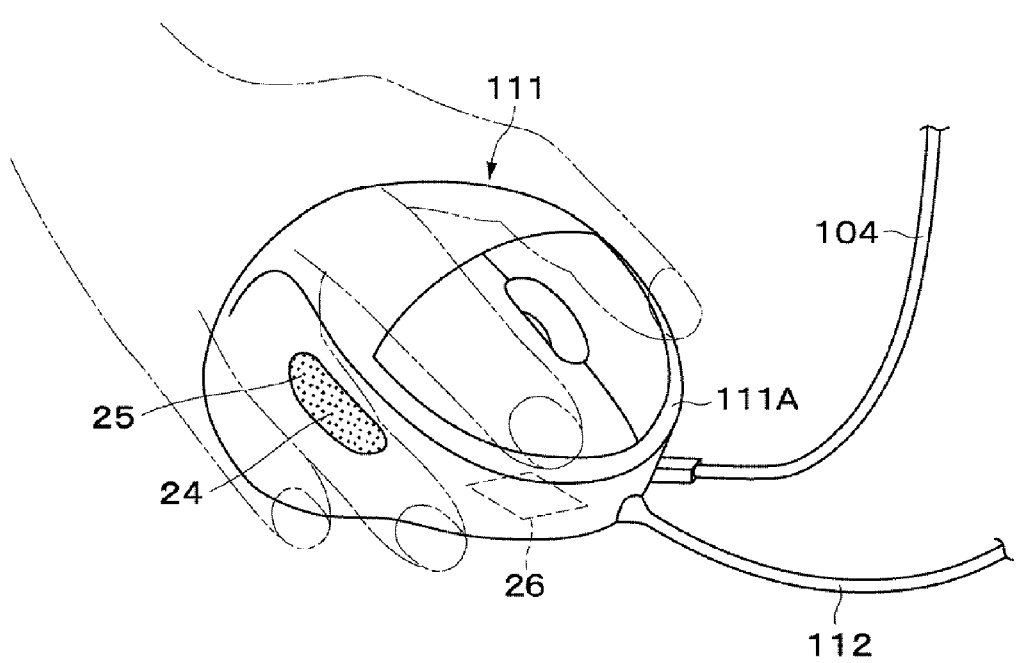
FIG. 24 is an explanatory view illustrating an electrocardiographic electrode in a biosensor device according to a modification.

Also, in the above-described seventh embodiment, the electrocardiographic electrode 24 is disposed in the casing 102A of the portable device 102. However, the present invention is not limited to such an arrangement. For example, as in a modification illustrated in FIG. 24, the electrocardiographic electrode 24 may be attached to a mouse 111, and the mouse 111 and a headphone (not shown in FIG. 24) may be connected to each other by a cable 104. The cable 104 is desirably attached to the mouse 111 in a detachable manner. In such a modification, the electrocardiographic electrode 24 is arranged, for example, in a portion of the mouse 111, i.e., the first portion for contact with the user, which portion is to be contacted with the medical finger of the right hand of the user operating the mouse 111. The processing circuit 26 may be mounted in a mouse casing 111A that is employed as the first housing. Alternatively, the processing circuit 26 may be installed as a processing program in a computer that is connected to the mouse 111 through another cable 112. This modification eliminates the necessity of attaching the portable device 102, etc. to the arm, for example, when the user performs the measurement while operating the computer.

While the biosensor devices 1, 41, 51, 61 and 101 according to the above-described embodiments use two light emitting elements 8 and 9 emitting the detection lights in the different wavelength ranges, the present invention is not limited to that case, and the light emitting elements may be disposed three or more. As an alternative, the number of light emitting elements may be one. When the number of light emitting elements is one, the function of measuring the oxygen saturation based on a difference in absorbance between oxygenated hemoglobin and deoxygenated hemoglobin is eliminated from the biosensor devices 1, 41, 51, 61 and 101.

Also, in the above-described embodiments, the reflected lights of two detection lights emitted from the light emitting elements 8 and 9 and having the different wavelength ranges are received by the light receiving element 10, and the photo-plethysmographic signal corresponding to the detection light emitted from the light emitting element 8 and the photo-plethysmographic signal corresponding to the detection light emitted from the light emitting element 9 are extracted from the optical detection signals corresponding to the reflected lights received by the light receiving element 10. However, the present invention is not limited to such an arrangement. For example, two light receiving elements may be disposed such that the photo-plethysmographic signal corresponding to the detection light emitted from the light emitting element 8 is extracted from the optical detection signal corresponding to the reflected light received by one of the two light receiving elements, and the photo-plethysmographic signal corresponding to the detection light emitted from the light emitting element 9 is extracted from the optical detection signal corresponding to the reflected light received by the other light receiving element.

Further, in the above-described embodiments, the light emitting elements 8 and 9 and the light receiving element 10 are disposed, by way of example, under the light transmissive electrocardiographic electrode 19 that is arranged on the upper surface of the housing 2 in the forward left portion thereof. However, the present invention is not limited to such an arrangement. The light emitting elements 8 and 9 and the light receiving element 10 may be disposed under the electrocardiographic electrode that is arranged on the upper surface of the housing 2 in the forward right portion thereof. In that case, the electrocardiographic electrode and the insulating film, which are disposed on the upper surface of the housing 2 in the forward right portion thereof, are formed respectively as a light transmissive electrocardiographic electrode and a light transmissive insulating film.

In the above-described embodiments, the light emitting elements 8 and 9, the light receiving element 10, and the surface-mounted components 11, 12 13 and 17 are sealed off by the light transmissive sealing member 18 or 42 on the base plate 7, and the light transmissive electrocardiographic electrode 19 or 43 and the light transmissive insulating film 20 or 46 are disposed on the light transmissive sealing member 18 or 42. However, the present invention is not limited to such an arrangement. For example, a light transmissive plate made of an insulating resin (e.g., a transparent insulating resin), which has optical transparency in the wavelength ranges of the lights emitted from the light emitting elements 8 and 9, may be disposed above the light emitting elements 8 and 9, the light receiving element 10, and the surface-mounted components 11, 12 13 and 17, and the light transmissive electrocardiographic electrode 19 or 43 and the light transmissive insulating film 20 or 46 may be disposed on an upper surface of the light transmissive plate. In that case, the light transmissive plate may be supported on the base plate 7 through a support member. Alternatively, the light transmissive plate may be mounted at the inner side or the upper side of the light passing opening 4B and fixed in place with respect to the light passing opening 4B by using, e.g., an adhesive.

In the above-described embodiments, the surface-mounted components 11, 12 and 13 of the light emitting element drive circuit 14, which includes the constant-current circuit and the high-frequency cut-off filter circuit, are arranged in surrounding relation to the light emitting elements 8 and 9. However, the present invention is not limited to such an arrangement. For example, other surface-mounted components for driving or controlling the light emitting elements 8 and 9, such as an overcurrent protective element in an overcurrent protective circuit, a high-frequency cutoff filter element in a high-frequency cutoff filter circuit, a coil, a diode, an operational amplifier, a switching element, and an IC, may be arranged in surrounding relation to the light emitting elements 8 and 9. When those other surface-mounted components are arranged as described above, the layout of each of the surface-mounted components on the base plate 7 is set such that a connection terminal of each surface-mounted component is disposed at a position opposing to the light emitting elements 8 and 9.

While the embodiments have been described above, by way of example, in connection with the portable biosensor devices 1, 41, 51, 61 and 101, the present invention is not limited to that case. For example, the biosensor device may be divided into a detection section and an arithmetic processing section. The detection section includes the components necessary for detecting the electrical signals relating to the electrocardiographic signal and the optical detection signal, such as the light emitting elements 8 and 9, the light receiving element 10, the surface-mounted components 11, 12 13 and 17 surrounding the light emitting elements 8 and 9 and the light receiving element 10, the peripheral wall reflector 16, the light transmissive sealing member 18, the light transmissive electrocardiographic electrode 19, and the light transmissive insulating film 20. The arithmetic processing section includes the components, such as the processing circuit 26 (except for the surface-mounted components 11, 12 13 and 17), necessary for executing signal processing on the electrical signals relating to the electrocardiographic signal and the optical detection signal, which are detected in the detection section, and executing the processing to generate the biological information. Further, the detection section is formed as a portable device, and the arithmetic processing section is formed as a desktop device, for example. In that case, the electrocardiographic electrode 24 and the insulating film 25 may be provided as part of the device formed as the detection section or part of the device formed as the arithmetic processing section. For example, when the electrocardiographic electrode 24 and the insulating film 25 are provided as part of the device formed as the arithmetic processing section, the electrocardiographic electrode 24 and the insulating film 25 are desirably constituted in the form of a capacitive-coupling electrocardiographic electrode probe, which is connectable to the device formed as the arithmetic processing section through a cord.

While the embodiments have been described above, by way of example, in connection with the case where the two electrocardiographic electrodes 19 and 24 are provided, the present invention is not limited to that case. For example, three or more electrocardiographic electrodes may be provided.

In the above-described embodiments, the thumbs of both the user's hands are brought into contact with the contact surfaces 20A, 46A and 25A of the insulating films 20, 46 and 25 of the electrocardiographic electrodes 19 and 24, and the electrical signals relating to the electrocardiographic signal and the optical detection signal relating to the photo-plethysmographic signal are detected from the thumbs. However, the present invention is not limited to that case. The electrical signals relating to the electrocardiographic signal and the optical detection signal relating to the photo-plethysmographic signal may be detected from other portions of the living body.

REFERENCE NUMBERS 1, 41, 51, 61, 101 biosensor device
7 base plate
8, 9 light emitting element (light emitter)
10 light receiving element (light receiver)
11, 12, 13, 17 surface-mounted component
16 peripheral wall reflector
19, 43 light transmissive electrocardiographic electrode
20, 46 light transmissive insulating film
20A, 25A, 46A contact surface
24 electrocardiographic electrode
25 insulating film
26 processing circuit
27 electrocardiographic signal detection unit
28, 29, 54, 64 electrocardiographic signal filter unit
32 photo-plethysmographic signal detection unit
36 arithmetic processing unit
55, 71 clamp circuit
55B, 71B diode (high-impedance element)
66, 81 first clamp circuit
66B, 81B diode (first high-impedance element)
67, 82 second clamp circuit
67B, 82B diode (second high-impedance element)
102 portable device
102A casing (first housing)
103 headphone
103A speaking casing (second housing)
104 cable
111 mouse
111A mouse casing (first housing)

The invention claimed is:

1. A biosensor device comprising:
at least one pair of electrocardiographic electrodes that detect electrical signals of a living body;
a respective insulating film disposed on each electrode of the at least one pair of electrocardiographic electrodes, each respective insulating film having a living body contact surface;
a light emitter configured to emit light to the living body;
a light receiver configured to receive reflected light from the living body; and
a processor circuit that generates an electrocardiographic signal by differentially amplifying the electrical signals of the living body, and generates a photo-plethysmographic signal based on the light emitted from the light emitter and the reflected light received by the light receiver, wherein at least one electrode of the at least one pair of electrocardiographic electrodes is a light transmissive electrocardiographic electrode comprising an electroconductive material having light transparency in a wavelength range of the light emitted from the light emitter, and the insulating film disposed on the light transmissive electrocardiographic electrode is a light transmissive insulating film comprising an insulating material having light transparency in the wavelength range of the light emitted from the light emitter.

2. The biosensor device according to claim 1, wherein the at least one pair of electrocardiographic electrodes detect electrical signals of a living body through capacitive coupling.

3. The biosensor device according to claim 1, wherein the processor circuit includes:
 an electrocardiographic signal detection unit that generates the electrocardiographic signal; and
 a photo-plethysmographic signal detection unit that generates the photo-plethysmographic signal.

4. The biosensor device according to claim 1, wherein the light emitter includes at least two light emitting elements that each emit light in different wavelength ranges.

5. The biosensor device according to claim 1, wherein the light emitter, the light receiver, and at least part of the processor circuit are mounted on a base plate.

6. The biosensor device according to claim 1, further comprising a peripheral wall reflector positioned around each of the light emitter and the light receiver.

7. The biosensor device according to claim 6, wherein the peripheral wall reflector is a solder fillet.

8. The biosensor device according to claim 3, further comprising:
 at least one clamp circuit including at least one high-impedance element connected to the electrocardiographic signal detection unit,
 wherein the at least one clamp circuit is configured such that a potential at a connected end of the at least one clamp circuit is held constant, and an impedance of the electrocardiographic signal detection unit at the connected end of the clamp circuit is larger than an impedance of the clamp circuit.

9. The biosensor device according to claim 1, wherein a first electrocardiographic electrode of the at least one pair of electrocardiographic electrodes and the processor circuit are contained in a first housing.

10. The biosensor device according to claim 9, wherein the respective insulating film covering the first electrocardiographic electrode contained in the first housing is exposed at a surface of the first housing.

11. The biosensor device according to claim 10, wherein a second electrocardiographic electrode of the at least one pair of electrocardiographic electrodes is contained in a second housing and is electrically connected to the processor circuit.

12. The biosensor device according to claim 11, wherein the respective insulating film covering the second electrocardiographic electrode contained in the second housing is exposed at a surface of the second housing.

13. The biosensor device according to claim 12, wherein the light emitter and the light receiver are contained in the second housing,
 the second electrocardiographic electrode is the light transmissive electrocardiographic electrode, and
 the respective insulating film disposed on the second electrocardiographic electrode is the light transmissive insulating film.

14. A biosensor device comprising:
 at least one pair of electrocardiographic electrodes that detect electrical signals of a living body;
 a respective insulating film disposed on each electrode of the at least one pair of electrocardiographic electrodes, each respective insulating film having a living body contact surface;
 at least two light emitting elements configured to each emit light in different wavelength ranges to the living body;
 a light receiver configured to receive reflected light from the living body;
 a processor circuit including an electrocardiographic signal detection unit that generates an electrocardiographic signal by differentially amplifying the electrical signals of the living body detected by the at least one pair of electrocardiographic electrodes, and a photo-plethysmographic signal detection unit that generates a photo-plethysmographic signal based on the light emitted from the light emitter and the reflected light received by the light receiver;
 a base plate on which the at least two light emitting elements, the light receiver, and at least part of the processor circuit are mounted;
 a peripheral wall reflector positioned around each of the at least two light emitting elements and the light receiver; and
 at least one clamp circuit including at least one high-impedance element connected to the electrocardiographic signal detection unit, wherein a potential at a connected end of the clamp circuit is held constant, and an impedance at the connected end of the electrocardiographic signal detection unit is larger than an impedance of the clamp circuit, wherein
 at least one electrode of the at least one pair of electrocardiographic electrodes is a light transmissive electrocardiographic electrode made of an electroconductive material having light transparency in a wavelength range of the light emitted from each of the at least two light emitting elements,
 the respective insulating film disposed on the light transmissive electrocardiographic electrode is a light transmissive insulating film made of an insulating material having light transparency in the wavelength range of the light emitted from each of the at least two light emitting elements.

15. The biosensor device according to claim 14, wherein the at least one pair of electrocardiographic electrodes detect electrical signals of a living body through capacitive coupling.

16. The biosensor device according to claim 14, wherein the peripheral wall reflector is a solder fillet.

* * * * *